US012709639B2

(12) United States Patent
Wiezorek

(10) Patent No.: US 12,709,639 B2
(45) Date of Patent: Aug. 18, 2026

(54) METHODS OF ADMINISTERING CHIMERIC ANTIGEN RECEPTOR IMMUNOTHERAPY

(71) Applicant: KITE PHARMA, INC., Santa Monica, CA (US)

(72) Inventor: Jeffrey S. Wiezorek, Santa Monica, CA (US)

(73) Assignee: Kite Pharma, Inc., Santa Monica, CA (US)

( * ) Notice: Subject to any disclaimer, the term of this patent is extended or adjusted under 35 U.S.C. 154(b) by 0 days.

(21) Appl. No.: 18/497,745

(22) Filed: Oct. 30, 2023

(65) Prior Publication Data

US 2024/0058381 A1 Feb. 22, 2024

Related U.S. Application Data

(63) Continuation of application No. 16/164,147, filed on Oct. 18, 2018, now abandoned.

(60) Provisional application No. 62/574,159, filed on Oct. 18, 2017.

(51) Int. Cl.

| | |
|---|---|
| ***C07K 14/725*** | (2006.01) |
| ***A61K 9/00*** | (2006.01) |
| ***A61K 31/573*** | (2006.01) |
| ***A61K 38/38*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***C07K 14/705*** | (2006.01) |
| ***C07K 16/24*** | (2006.01) |
| *A61K 38/18* | (2006.01) |
| *A61K 38/19* | (2006.01) |
| *A61K 38/31* | (2006.01) |
| *A61K 38/34* | (2006.01) |
| *A61K 38/35* | (2006.01) |
| *A61K 39/00* | (2006.01) |

(52) U.S. Cl.

CPC ........ *C07K 14/7051* (2013.01); *A61K 9/0019* (2013.01); *A61K 40/11* (2025.01); *A61K 40/31* (2025.01); *A61K 40/4211* (2025.01); *A61P 35/00* (2018.01); *C07K 16/248* (2013.01); *A61K 31/573* (2013.01); *A61K 38/1816* (2013.01); *A61K 38/193* (2013.01); *A61K 38/31* (2013.01); *A61K 38/34* (2013.01); *A61K 38/35* (2013.01); *A61K 38/38* (2013.01); *A61K 2039/804* (2018.08); *A61K 2239/31* (2023.05); *A61K 2239/38* (2023.05); *A61K 2239/48* (2023.05)

(58) Field of Classification Search

None

See application file for complete search history.

(56) References Cited

U.S. PATENT DOCUMENTS

| | | | |
|---|---|---|---|
| 4,946,778 | A | 8/1990 | Ladner et al. |
| 5,091,513 | A | 2/1992 | Huston et al. |
| 5,132,405 | A | 7/1992 | Huston et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,591,827 | A | 1/1997 | Brakenhoff et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 5,728,388 | A | 3/1998 | Terman |
| 5,827,642 | A | 10/1998 | Riddell et al. |
| 5,830,462 | A | 11/1998 | Crabtree et al. |
| 5,834,266 | A | 11/1998 | Crabtree et al. |
| 5,869,337 | A | 2/1999 | Crabtree et al. |
| 6,040,177 | A | 3/2000 | Riddell et al. |
| 6,165,787 | A | 12/2000 | Crabtree et al. |
| 6,319,494 | B1 | 11/2001 | Capon et al. |
| 6,410,319 | B1 | 6/2002 | Raubitschek et al. |
| 6,797,514 | B2 | 9/2004 | Berenson et al. |
| 6,867,041 | B2 | 3/2005 | Berenson et al. |

(Continued)

FOREIGN PATENT DOCUMENTS

| | | |
|---|---|---|
| CN | 103820393 | 5/2014 |
| CN | 106701827 | 5/2017 |

(Continued)

OTHER PUBLICATIONS

Locke et al. Updated Phase 1 Results from ZUMA-1: A Phase 1-2 Multi-Center Study Evaluating the Safety and Efficacy of KTE-C19 (Anti-CD19 CAR T Cells) in Subjects with Refractory Aggressive Non-(Molecular Therapy vol. 24 supplement 1, May 2016 No. 745) (Year: 2016).*

Locke 2017 Phase 1 Results of ZUMA-1: A Multicenter Study of KTE-C19 Anti-CD19 CAR T Cell Therapy in Refractory Aggressive Lymphoma (Molecular Therapy vol. 25 No. 1 Jan. 2017 (Year: 2017).*

Lee et alCurrent concepts in the diagnosis and management of cytokine release syndrome (Blood Jul. 10, 2014, vol. 124, No. 2) (Year: 2014).*

Park Adoptive Transfer of Chimeric Antigen Receptor Re-directed Cytolytic T Lymphocyte Clones in Patients with Neuroblastoma (Molecular Therapy vol. 15 No. 4, Apr. 2007) (Year: 2007).*

Decision of Final Rejection for Japanese Application No. 2020-521585 dated Apr. 18, 2023. 9 pages.

(Continued)

*Primary Examiner* — Daniel E Kolker

*Assistant Examiner* — Brian Hartnett

(74) *Attorney, Agent, or Firm* — Sheppard Mullin Richter & Hampton LLP

(57) ABSTRACT

The disclosure provides cells comprising CD19-directed chimeric antigen receptor (CAR) genetically modified autologous T cell immunotherapy for the treatment of, e.g., relapsed or refractory large B-cell lymphoma after two or more lines of systemic therapy, including diffuse large B-cell lymphoma (DLBCL) not otherwise specified, primary mediastinal large B-cell lymphoma, high grade B-cell lymphoma, and DLBCL arising from follicular lymphoma. Some aspects of the disclosure relate to methods of treatment and monitoring following infusion of T cell therapy provided herein.

15 Claims, No Drawings

(56) References Cited

U.S. PATENT DOCUMENTS

| | | | |
|---|---|---|---|
| 6,905,874 | B2 | 6/2005 | Berenson et al. |
| 7,709,226 | B2 | 5/2010 | Foote |
| 7,741,465 | B1 | 6/2010 | Eshar et al. |
| 8,211,422 | B2 | 7/2012 | Eshhar et al. |
| 8,486,693 | B2 | 7/2013 | Park et al. |
| 8,562,991 | B2 | 10/2013 | Igawa et al. |
| 8,679,492 | B2 | 3/2014 | Blein et al. |
| 9,296,820 | B2 | 3/2016 | Umana et al. |
| 9,834,590 | B2 | 12/2017 | Campana et al. |
| 9,855,298 | B2 | 1/2018 | Bot et al. |
| 9,987,308 | B2 | 6/2018 | Riddell et al. |
| 10,221,245 | B2 | 3/2019 | Brogdon et al. |
| 10,287,350 | B2 | 5/2019 | Kochenderfer |
| 10,493,139 | B2 | 12/2019 | Wu et al. |
| 11,723,923 | B2 | 8/2023 | Perez et al. |
| 11,793,834 | B2 | 10/2023 | Perez et al. |
| 2002/0006409 | A1 | 1/2002 | Wood |
| 2004/0126363 | A1 | 7/2004 | Jensen et al. |
| 2007/0014720 | A1 | 1/2007 | Gazit-Bornstein et al. |
| 2010/0104509 | A1 | 4/2010 | King et al. |
| 2011/0286980 | A1 | 11/2011 | Brenner |
| 2012/0093842 | A1 | 4/2012 | Eshhar et al. |
| 2012/0130076 | A1 | 5/2012 | Holt et al. |
| 2012/0213783 | A1 | 8/2012 | Rosenberg et al. |
| 2013/0266551 | A1 | 10/2013 | Campana et al. |
| 2013/0287748 | A1 | 10/2013 | June et al. |
| 2014/0050708 | A1 | 2/2014 | Powell et al. |
| 2014/0099309 | A1 | 4/2014 | Powell et al. |
| 2014/0134195 | A1 | 5/2014 | Russell |
| 2014/0154228 | A1 | 6/2014 | Volk et al. |
| 2014/0171649 | A1 | 6/2014 | Li et al. |
| 2014/0227237 | A1 | 8/2014 | June et al. |
| 2014/0271635 | A1 | 9/2014 | Brogdon et al. |
| 2014/0286934 | A1 | 9/2014 | Blein et al. |
| 2014/0286987 | A1 | 9/2014 | Spencer et al. |
| 2015/0038684 | A1 | 2/2015 | Jensen |
| 2015/0202286 | A1 | 7/2015 | June et al. |
| 2015/0266973 | A1 | 9/2015 | Jarjour et al. |
| 2015/0283178 | A1 | 10/2015 | June et al. |
| 2015/0344844 | A1 | 12/2015 | Better et al. |
| 2016/0009813 | A1 | 1/2016 | Themeli et al. |
| 2016/0046700 | A1 | 2/2016 | Foster et al. |
| 2017/0173080 | A1 | 6/2017 | Lee et al. |
| 2017/0368098 | A1 | 12/2017 | Chen et al. |
| 2018/0355052 | A1 | 12/2018 | Orentas et al. |
| 2018/0371093 | A1 | 12/2018 | Bilic et al. |
| 2019/0119638 | A1 | 4/2019 | Sadelain et al. |
| 2019/0151361 | A1 | 5/2019 | Wiezorek |
| 2019/0358262 | A1 | 11/2019 | Albertson |
| 2019/0359697 | A1 | 11/2019 | Young et al. |
| 2019/0388471 | A1 | 12/2019 | June et al. |
| 2020/0002400 | A1 | 1/2020 | Yao et al. |
| 2020/0283729 | A1 | 9/2020 | Loew et al. |
| 2021/0145304 | A1 | 5/2021 | Visweswara et al. |
| 2021/0147569 | A1 | 5/2021 | Press et al. |
| 2022/0160729 | A1 | 5/2022 | Deisher |
| 2022/0281976 | A1 | 9/2022 | Rosenthal et al. |
| 2022/0387492 | A1 | 12/2022 | Bot et al. |
| 2022/0389449 | A1 | 12/2022 | Paul et al. |
| 2023/0255962 | A1 | 8/2023 | Boiko et al. |
| 2023/0374105 | A1 | 11/2023 | Bitter et al. |
| 2024/0018256 | A1 | 1/2024 | Chen et al. |
| 2024/0058381 | A1 | 2/2024 | Wiezorek |
| 2024/0082307 | A1 | 3/2024 | Bot et al. |
| 2024/0115611 | A1 | 4/2024 | Perez et al. |
| 2024/0252538 | A1 | 8/2024 | Brannetti et al. |
| 2024/0279665 | A1 | 8/2024 | Zhao et al. |
| 2025/0002579 | A1 | 1/2025 | Cooper et al. |

FOREIGN PATENT DOCUMENTS

| | | | |
|---|---|---|---|
| CN | 108384760 A | 8/2018 | |
| WO | WO 2007002223 | 1/2007 | |
| WO | WO-2008/081035 A1 | 7/2008 | |
| WO | WO 2009091826 | 7/2009 | |
| WO | WO-2012033885 | 3/2012 | |
| WO | WO-2012/07900 A1 | 6/2012 | |
| WO | WO 2012079000 | 6/2012 | |
| WO | WO-2012/12954 A1 | 9/2012 | |
| WO | WO 2012138475 | 10/2012 | |
| WO | WO 2013/123061 A1 | 8/2013 | |
| WO | WO 2013154760 | 10/2013 | |
| WO | WO 2014055657 | 4/2014 | |
| WO | WO 2014127261 | 8/2014 | |
| WO | WO 2014153270 | 9/2014 | |
| WO | WO 2014184744 | 11/2014 | |
| WO | WO 2014186469 | 11/2014 | |
| WO | WO 2015075468 | 5/2015 | |
| WO | WO 2015080981 | 6/2015 | |
| WO | WO 2015090229 | 6/2015 | |
| WO | WO 2015120096 | 8/2015 | |
| WO | WO-2015120096 A2 * | 8/2015 | ............ A61K 35/17 |
| WO | WO 2016044745 | 3/2016 | |
| WO | WO 2016090369 | 6/2016 | |
| WO | WO 2016/210293 A1 | 12/2016 | |
| WO | WO 2017/025038 A1 | 2/2017 | |
| WO | WO 2017015783 | 2/2017 | |
| WO | WO 2017/222593 A1 | 12/2017 | |
| WO | WO 2018145648 | 8/2018 | |
| WO | WO 2018161017 | 9/2018 | |
| WO | WO 2018213337 | 11/2018 | |

OTHER PUBLICATIONS

Examination Report for Australian Application No. 2021282551 dated Dec. 14, 2022. 4 pages.

Examination Report for Australian Application No. 2021282551 dated Nov. 7, 2022. 5 pages.

Galon, Journal of Clinical Oncology (May 2017), vol. 35, No. 15 suppl., abstract 3025, ascopubs.org/doi/10.1200/JCO.2017.35.15_suppl.3025. 4 pages.

Notice of Final Rejection for Korean Application No. 10-2020-7013686 dated Oct. 6, 2022. 8 pages.

Office Action and Search Report for Chinese Application No. 201880067426.5 dated Feb. 4, 2023. 13 pages.

Office Action for Japanese Application No. 2020-521585 dated Oct. 25, 2022. 8 pages.

Office Action with Search Report for Taiwan Application No. 107136797 dated Sep. 15, 2022. 12 pages.

Examination Report for Australian Patent Application No. 2021282551 dated Jul. 29, 2022. 5 pages.

Examination Report for Australian Patent Application No. 2021282551 dated May 9, 2022. 4 pages.

Notice of Final Rejection Korean for Patent Application No. 10-2020-7013686 dated Jun. 3, 2022. 7 pages.

Office Action for Canadian Patent Application No. 3,084,470 dated Mar. 23, 2022. 4 pages.

Official Action for Argentinian Patent Application No. 20180103032 dated Feb. 15, 2022. 9 pages.

Examination Report for Australia Patent Application No. 2018351046 dated Nov. 17, 2021. 4 pages.

Notice of Preliminary Rejection for Korean Patent Application No. 10-2020-7013686 dated Oct. 14, 2021. 13 pages.

Brudno et al. Toxicities of chimeric antigen receptor T cells: recognition and management. Blood, Jun. 30, 2016, vol. 127, No. 26 (Year: 2016).

Locke et al. Phase 1 Results of ZUMA-1: A Multicenter Study of KTE-C19 Anti-CD19 CAR T Cell Therapy in Refractory Agressive Lymphoma. Molecular Therapy vol. 25 No. 1 Jan. 2017 (Year: 2017).

Gust et al. Endothelial Activation and Blood-Brain Barrier Disruption in Neurotoxicity after Adoptive Immunotherapy with CD19 CAR-T Cells. Published OnlineFirst Oct. 12, 2017; DOI: 10.1158/2159-8290.CD-17-0698. (Year: 2017).

Examination Report issued on Canadian application counterpart 3,084,470, mailed Mar. 23, 2021.

Locke et al., Abstract CT019: Primary results from ZUME-1: a pivotal trial of axicabtagene ciloleucel (axicel; KTEC19) in patients

(56) References Cited

OTHER PUBLICATIONS with refractory aggressive non-Hodgkin lymphoma (NHL); Cancer research vol. 77/Supplement 13/CT019.
Lee et al. Current concepts in the diagnosis and management of cytokine release syndromeBLOOD, Jul. 10, 2014 x vol. 124 , No. 2 (Year: 2014).
Locke et al. Updated Phase 1 Results from ZU MA-1. Molecular Therapy vol. 24, Supplement 1, May 2016 (Year: 2016).
Lu et al. A Rapid Cell Expansion Process for Production of Engineered Autologous CAR-T Cell Therapies. Hu Man Gene Therapy Methods, vol. 27 No. 6: 2016 (Year: 2016).
Park et al. Adoptive Transfer of Chimeric Antigen Receptor Re-directed Cytolytic T Lymphocyte Clones in Patients with Neuroblastoma. (Year: 2007).
Examination Report dated Dec. 16, 2020 for counterpart Australian Patent Application No. 2018351046.
Intl. Search Report-Written Opinion dated Feb. 4, 2019 for Intl. Appl. No. PCT/US2018/056467.
Intl. Preliminary Report on Patentability-Written Opinion dated Apr. 21, 2020 for Intl. Appl. No. PCT/US2018/056467.
Kochenderfer mmunother., et 32(7): al., 689-702 "Construction (2009) and Pre-clinical Evaluation of an Anti-CD19 Chimeric Antigen Receptor", J immunother., 32(7): 689-702 (2009).
Ruella et al., "Chimeric Antigen Receptor T cells for B Cell Neoplasms: Choose the Right CAR for You", Curr Hematol Malig Rep, 11:368-384 (2016).
Sadelain et al, "The Basic Principles of Chimeric Antigen Receptor Design", Cancer Discovery, 3:388-398 (2013).
Frederick L. Locke et al., "Phase 1 Results of ZUMA-1: A Multi-center Study of KTE-C19 Anti-CD19 CAR T Cell Therapy in Refractory Aggressive Lymphoma", Molecular Therapy, Jan. 2017, pp. 285-295, vol. 25, No. 1.
J. N. Kochenderfer et al., "Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor", J. Clinical Oncology, Aug. 25, 2014, pp. 540-549, vol. 33, No. 6.
Jennifer N. Brudno et al., "Toxicities of Chimeric Antigen Receptor T Cells: Recognition and Management," Blood, May 20, 2016 (online), pp. 3321-3330, vol. 127, No. 26.
Tangying Lily Lu et al., "A Rapid Cell Expansion Process for Production of Engineered Autologous CAR-T Cell Therapies", Human Gene Therapy Methods, 2016, pp. 209-218, vol. 27, No. 6.
Marcus P. Watkins et al., "CD19-targeted Immunotherapies for Treatment of Patients with non-Hodgkin B-cell Lymphomas", Expert Opinion on Investigational Drugs, 2018., pp. 601-611, vol. 27, No. 7.
Sattva S. Neelapu et al., "Axicabtagene Ciloleucel CAR T-Cell Therapy in Refractory Large B-Cell Lymphoma", The New England Journal of Medicine, Dec. 28, 2017, pp. 2531-2544, vol. 377, No. 26.
Highlights of Prescribing Information for ACTEMRA® (tocilizumab) Aug. 2017. 43 pages.
Jensen, et al. Antitransgene rejection responses contribute to attenuated persistence of adoptively transferred CD20/CD19-specific chimeric antigen receptor redirected T cells in humans. Biology of blood and marrow transplantation. 16.9 (2010): 1245-1256.
Whitlow, et al. An improved linker for single-chain Fv with reduced aggregation and enhanced proteolytic stability. Protein Engin. 1993; 6(8):989-995.
Abramson et al., High Durable CR Rates in Relapsed/Refractory (R/R) Aggressive B-NHL Treated with the CD19-Directed Car T Cell Product JCAR017 (Transcend NHL 001): Defined Composition Allows for Dose-Finding and Definition of Pivotal Cohort, Blood 2017, vol. 130, Supplement 1, p. 581.
Al-Lazikani et al., "Standard conformations for the canonical structures of immunoglobulins" J Mol Bioi 273: 927-948 (1997).
Akbar et al., "A compact vocabulary of paratope-epitope interactions enables predictability of antibody-antigen binding," Cell Reports, 34 pp. 1-21 (Year: 2021).
Alabanza et al., "Function of Novel Anti-CD19 Chimeric Antigen Receptors with Human Variable Regions Is Affected by Hinge and Transmembrane Domains," Mol. Ther., 25(11), 2452-2465 (Epub Jul. 2017. 27).
Ando et al., A Safeguard System for Induced Pluripotent Stem Cell-Derived Rejuvenated T Cell Therapy, Stem Cell Reports 2015, vol. 5, pp. 597-608.
Arnon et al., "Monoclonal Antibodies and Cancer Therapy", pp. 243-256, Alan R. Liss, Inc. (1985).
Barbas et al., "Recombinant human Fab fragments neutralize human type 1 immunodeficiency virus in vitro", Proc. Natl. Acad. Sci. USA, 89(19): 9339-43 (1992).
Beatty et al., "Mesothelin-specific chimeric antigen receptor mRNA-engineered T cells induce antitumor activity in solid malignancies," Cancer Immunology Research, 2(2), 112-120 (2014).
Bhojwani et al. (2018), "Inotuzumab ozogamicin in pediatric patients with relapsed/refractory acute lymphoblastic leukemia", Leukemia, Acute lymphoblastic leukemia, accessed at https://doi.org/10.1038/s41375-018-0265-z, 1-9.
Bodogai et al. Anti-CD20 Antibody Promotes Cancer Escape via Enrichment of Tumor-Evoked Regulatory B Cells Expressing Low Levels of CD20 and CD137L. Cancer Res 73(7): 2127-2138, 2013.
Borowitz et al. (2015), "Prognostic significance of minimal residual disease in high risk B-ALL: a report from Children's Oncology Group study AALL0232", Blood, 126(8), 964-971.
Brentjens et al., "CD19-targeted T cells rapidly induce molecular remissions in adults with chemotherapy-refractory acute lymphoblastic leukemia," Science Translational Medicine, 5(177), 177ra38 (2013), 19 pages, Author Manuscript.
Brentjens et al., "Eradication of systemic B-cell tumors by genetically targeted human T lymphocytes co-stimulated by COBO and interleukin-15," Nature Medicine, 9(3), 279-286 (2003).
Brentjens et al., "Genetically targeted T cells eradicate systemic acute lymphoblastic leukemia xenografts," Clinical Cancer Research, 13(18), 5426-5435 (2007).
Brentjens et al., "Novel cellular therapies for leukemia: CAR-modified T cells targeted to the CD19 antigen," Hematology. American Society of Hematology. Education Program, 2012, 143-151 (2012).
Brentjens et al., "Safety and persistence of adoptively transferred autologous CD19-targeted T cells in patients with relapsed or chemotherapy refractory B-cell leukemias," Blood, 118 (18), 4817-4828 (2011).
Brudno et al., "Clinical anti-lymphoma activity and toxicity of T cells expressing a novel anti-CD19 chimeric antigen receptor with fully-human variable regions," ASCO Meeting Library, abstract cited in J Clin Oncol., 36, 2018 (suppl; abstr 3052).
Brudno et al., Allogeneic T Cells That Express an Anti-CD19 Chimeric Antigen Receptor Induce Remissions of B-Cell Malignancies That Progress After Allogeneic Hematopoietic Stem-Cell Transplantation Without Causing Graft-Versus-Host Disease, Journal of Clinical Oncology 2016, vol. 34, No. 10, pp. 1112-1121.
Brudno et al., Chimeric antigen receptor T-cell therapies for lymphoma, Nature Reviews Clinical Oncology 2018, vol. 15, pp. 31-46.
BRüggemann et al. (2017), "Minimal residual disease in adult ALL: technical aspects and implications for correct clinical interpretation", Blood Advances, 1(25), 2456-2466.
Burns et al., "Vesicular stomatitis virus G glycoprotein pseudotyped retroviral vectors: concentration to very high titer and efficient gene transfer into mammalian and non mammalian cells," Proc. Natl. Acad. Sci., USA, 90 (17), 8033-8037 (1993).
Cannarile et al. (2017), "Colony-stimulating factor 1 receptor (CSF1R) inhibitors in cancer therapy", Journal for Immuno Therapy of Cancer, 5(53), 1-13.
Cao et al., Anti-CD19 Chimeric Antigen Receptor T Cells in Combination With Nivolumab Are Safe and Effective Against Relapsed/Refractory B-Cell Non-hodgkin Lymphoma, Frontiers in Oncology 2019, vol. 9, article 767.
Cartellieri et al., Chimeric Antigen Receptor-Engineered T Cells for Immunotherapy of Cancer. Journal of Biomedicine and Biotechnology 2010, XP055206629, doi:10.1155/2010/956304. 13 pages.
Casan et al. Anti-CD20 monoclonal antibodies: reviewing a revolution. Human Vaccines Immunother 14(12): 2820-2841, 2018.

(56) References Cited

OTHER PUBLICATIONS

Champe et al., "Monoclonal Antibodies That Block the Activity of Leukocyte Function-associated Antigen 1 Recognize Three Discrete Epitopes in the Inserted Domain of CD11a", J Biol Chem, 270(3): 1388-94 (1995).
Chayen, "The role of oil in macromolecular crystallization", Structure, 5(10): 1269-1274 (1997).
Cheadle et al., "Natural expression of the CD19 antigen impacts the long-term engraftment but not antitumor activity of CD19-specific engineered T cells," Journal of Immunology, 184 (4), 1885-1896 (2010).
Chen et al., Anti-CD19 Chimeric Antigen Receptor T Cells Improve Responses to Chemotherapy- Refractory Mantle Cell Lymphoma: A Case Report, Blood 2016, vol. 128, No. 22: 5393, DOI: 10.1182/blood.V128.22.5393.5393. 2 pages.
Chen et al., Discovery of Small-Molecule Inhibitors of Hcv NS3-4A Protease as Potential Therapeutic Agents against HCV Infection. Current Medicinal Chemistry 2005, vol. 12, No. 20, doi: 10.2174/0929867054864769, pp. 2317-2342, XP009110972.
Cheson et al. (2007), "Revised Response Criteria for Malignant Lymphoma", Journal of Clinical Oncology, 25(5), 579-586.
Cheson et al. (2014), "Recommendations for Initial Evaluation, Staging, and Response Assessment of Hodgkin and Non-Hodgkin Lymphoma: The Lugano Classification", Journal of Clinical Oncology, 1-10.
Cheung et al., "Epitope-specific antibody response to the surface antigen of duck hepatitis B virus in infected ducks", Virology 176(2): 546-552 (1990).
Cho et al. Monoclonal Antibody: A New Treatment Strategy against Multiple Myeloma. Antibodies 6: 18, 2017, doi:10.3390/antibod6040018 (22 total pages).
Chothia et al., "Canonical structures for the hypervariable regions of immunoglobulins", J Mol Biol, 196: 901-917 (1987).
Chothia et al., "Structural repertoire of the human VH segments" J Mol Biol, 227: 799-817 (1992).
Cole et al., In: "Monoclonal Antibodies and Cancer Therapy", Alan R. Liss, Inc., pp. 77-96 (1985).
Cooper et al., "T-cell clones can be rendered specific for CD19: toward the selective augmentation of the graft-versus-B-lineage leukemia effect," Blood, 101 (4), 1637-1644 (2003).
Cote et al., Generation of human monoclonal antibodies reactive with cellular antigens, Proc Natl Acad Sci USA, 80 (7): 2026-2030 (1983).
Crotta et al. (2018), "Survival after stem-cell transplant in pediatric and young-adult patients with relapsed and refractory B-cell acute lymphoblastic leukemia", Curr Med Resin, Opin., 34, 1-18.
Cunningham et al., "High-resolution epitope mapping of hGH-receptor interactions by alanine-scanning mutagenesis", Science 244(4908): 1081-85 (1989).
Dayhoff et al., "Atlas of Protein Sequence and Structure: A Model of Evolutionary Change in Proteins", 5: 345-352 (1978).
Deangelo et al. (2017), "32nd Annual Meeting and Pre-Conference Programs of the Society for Immunotherapy of Cancer (SITC 2017): Part One," Journal for Immuno Therapy of Cancer, 5 (Suppl 2)(86), P217.
Devereux et al., "A comprehensive set of sequence analysis programs for the VAX", Nucl. Acid Res., 12: 387-395 (1984).
Dolmans et al. (2003), "Photodynamic therapy for cancer", Nature Reviews, Cancer, 3, 380-397.
Enblad et al., A Phase I/IIa Trial Using CD19-Targeted Third-Generation Car T Cells for Lymphoma and Leukemia, Clinical Cancer Research 2018, vol. 24, No. 24, pp. 6185-6194, DOI: 10.1158/1078-0432.CCR-18-0426.
Eshhar et al., "Tumor-specific T-bodies: towards clinical application", Cancer Immunol Immunotherapy, 45(3-4):131-136 (1997).
Examination Report for Australian Application No. 2019397033 dated Mar. 9, 2023. 5 pages.
Examination Report for New Zealand Application No. 777087 dated Nov. 20, 2023. 3 pages.
Examiner Requisition for Canadian Application No. 3,122,762 dated Jul. 29, 2022. 4 pages.
Fegan et al. "Chemically controlled protein assembly: techniques and applications", Chem. Rev., 110(6): 3315-3336 (2010).
Finney et al., "Chimeric receptors providing both primary and costimulatory signaling in T cells from a single gene product", Journal of Immunology, 161(6): (1998), Abstract only.
First Examination Report dated Sep. 2, 2021 in GCC Appl. No. GC 2019-38820.
Fishwild et al., "High-avidity human lgG kappa monoclonal antibodies from a novel strain of minilocus transgenic mice." Nature Biotechnology, 14(7): 845-51 (1996).
Fraietta et al., Determinants of response and resistance to CD19 chimeric antigen receptor (Car) T cell therapy of chronic lymphocytic leukemia, Nature Medicine 2018, vol. 24, pp. 563-571.
Frey et al. (2019), "Optimizing Chimeric Antigen Receptor T-Cell Therapy for Adults With Acute Lymphoblastic Leukemia", Journal of Clinical Oncology, 1-10.
Gen Bank Accession No. ADM64594.1, published Jun. 11, 2012.
Giege et al., "Crystallogenesis of biological macromolecules: facts and perspectives", Acta Crystallogr D Biol Crystallogr, 50(Pt 4): 339-350 (1994).
Gilead Sciences Announces Fourth Quarter and Full Year 2018 Financial Results?Gilead?Feb. 4, 2019?https://s24.q4cdn.com/804398512/files/doc_news/archive/829f46cd-0ddb-43d5-bedb-3771670d8102.pdf.
Gross et al., "Therapeutic Potential of T Cell Chimeric Antigen Receptors (CARs) in Cancer Treatment: Counteracting Off-Tumor Toxicities for Safe CART Cell Therapy", Annu. Rev. Pharmacol. Toxicol., 56: 59-83 (2016).
Grupp et al., "Chimeric antigen receptor-modified T cells for acute lymphoid leukemia," New England Journal of Medicine, 368 (16), 1509-1518 (2013).
Guedan et al., "Engineering and Design of Chimeric Antigen Receptors," Molecular Therapy: Methods & Clinical Development, 2019, vol. 12, pp. 145-156.
Gupta et al. (2018), "Flow-cytometric vs. —morphologic assessment of remission in childhood acute lymphoblastic leukemia: a report from the Children's Oncology Group (COG)", Leukemia, Springer Nature, accessed at https://doi.org/10.1038/s41375-018-0039-7, 1-10.
Gust et al., Endothelial Activation and Blood-Brain Barrier Disruption in Neurotoxicity after Adoptive Immunotherapy with CD19 Car-T Cells. Cancer Discovery 2017, 7(12), pp. 1404-1419.
Hamilton, "Gm-Csf as a target in inflammatory/autoimmune disease: current evidence and future therapeutic potential", Expert Reviews, Clin. Immunol., 2015, Early online, accessed at 10.1586/1744666X.2015.1024110, 1-9.
Hay et al., Chimeric Antigen Receptor (Car) T Cells: Lessons Learned from Targeting of CD19 in B-Cell Malignancies. Drugs 2017, doi 10.1007/s40265-017-0690-8. 16 pages.
Hellstrom et al., "Antibodies For Drug Delivery", in Controlled Drug Delivery (2nd Ed.), Robinson et al. (eds.), Marcel Dekker, Inc., (1987), Abstract only.
Henikoff et al., "Amino acid substitution matrices from protein blocks", Proc. Natl. Acad. Sci. U.S.A., 89(22): 10915-10919 (1992).
Hermans et al., "The vital assay: a versatile fluorometric technique for assessing CTL- and NKT-mediated cytotoxicity against multiple targets in vitro and in vivo," Journal of Immunological Methods, 285 (1), 25-40 (2004).
Highlights of Prescribing Information for Actemra R (tocilizumab), 2017, 43 pages.
Highlights of Prescribing Information for YESCARTA (axicabtagene ciloleucel), 2017, 31 pages.
Hirayama et al., The response to lymphodepletion impacts PFS in patients with aggressive non-Hodgkin lymphoma treated with CD19 Car T cells, Blood 2019, vol. 133, No. 17, pp. 1876-1887.
Hombach et al., "Costimulation by chimeric antigen receptors revisited the T cell antitumor response benefits from combined CD28-OX40 signalling," International Journal of Cancer, 129 (12), 2935-2944 (2011).

(56) References Cited

OTHER PUBLICATIONS

Hoogenboom et al., By-passing immunisation: Human antibodies from synthetic repertoires of germline VH gene segments rearranged in vitro, J. Mol. Biol., 227(2): 381-388 (1991).
Hunger et al. (2015), "Acute Lymphoblastic Leukemia in Children", The New England Journal of Medicine, 373(16), 1541-1552.
Huston et al., "Protein engineering of antibody binding sites: recovery of specific activity in an anti-digoxin single-chain Fv analogue produced in Escherichia coli", Proc Nat Acad Sci USA 85(16):5879- 5883 (1988).
International Search Report and Written Opinion for International Application No. PCT/US2020/059285 dated Apr. 12, 2021. 9 pages.
International Search Report and Written Opinion for International Application No. PCT/US2019/065776 dated Jun. 24, 2020. 21 pages.
Jaffe et al., "Understanding the New WHO Classification of Lymphoid Malignancies: Why It's Important and How It Will Affect Practice," American Society of Clinical Oncology, 2017, vol. 37, pp. 535-546.
Jain et al. (2019), "Mantle cell lymphoma: 2019 update on the diagnosis, pathogenesis, prognostication, and management", Annual Clinical Updates in Hematological Malignancies, 94, 710-725.
Jain et al., Axicabtagene ciloleucel (KTE-C19), an anti-CD19 Car T therapy for the treatment of relapsed/refractory aggressive B-cell non-Hodgkin's lymphoma, Therapeutics and Clinical Risk Management 2018, vol. 14, pp. 1007-1017.
Jena et al., Redirecting T-cell specificity by introducing a tumor-specific chimeric antigen receptor. Blood 2010; vol. 116, No. 7, pp. 1035-1044, XP055021403.
Juo, Pei-Show (2002) "Concise dictionary of biomedicine and molecular biology." second edition, Library of Congress Cataloging-in-Publication Data, CRC Press, 1163.
Kabat et al., "Attempts to locate complementarity-determining residues in the variable positions of light and heavy chains", Ann NY Acad Sci, 190: 382-391 (1971).
Kalos et al., T cells with chimeric antigen receptors have potent antitumor effects and can establish memory in patients with advanced leukemia, Sci. Transl. Med., 3(95): 95ra73 (2011).
Kantarjian et al. (2017), "Blinatumomab versus Chemotherapy for Advanced Acute Lymphoblastic Leukemia", The New England Journal of Medicine, 376(9), 836-847.
Kapoor et al. Anti-CD20 monoclonal antibody therapy in multiple myeloma. Brit J Haematol 141: 135-148, 2008.
Kirkland et al., "Analysis of the fine specificity and cross-reactivity of monoclonal anti-lipid A antibodies", J. Immunol. 137(11), 3614-2619, (1986).
Kite, A Gilead Company, "A Sutdy Evaluating the Safety and Efficacy of Brexucabtagene Autoleucel (KTE-X19) in Adult Subjects with Relapsed/Refractory B-precursor Acute Lymphoblastic Leukemia (ZUMA-3)", ClinicalTrials.gov, Trial No. NCT02614066, Dec. 3, 2018 (Mar. 12, 2018).
Klein et al., "Epitope interactions of monoclonal antibodies targeting CD20 and their relationship to functional properties," mAbs 5:1, pp. 22-33 (Year: 2013).
Kochenderfer et al. (2017), "Lymphoma Remissions Caused by Anti-CD19 Chimeric Antigen Receptor T Cells Are Associated With High Serum Interleukin-15 Levels", Journal of Clinical Oncology, 35(16), 1803-1813.
Kochenderfer et al., "B-cell depletion and remissions of malignancy along with cytokine-associated toxicity in a clinical trial of anti-CD19 chimeric-antigen-receptor-transduced T cells," Blood, 119(12), 2709-2720 (2012).
Kochenderfer et al., "Eradication of B-lineage cells and regression of lymphoma in a patient treated with autologous T cells genetically engineered to recognize CD19," Blood, 116 (20), 4099-4102 (2010).
Kochenderfer et al., "Treating B-cell cancers with T cells expressing anti CD19 chimeric antigen receptors," Nature Reviews. Clinical Oncology, 10(5), 267-276 (2013).
Kozbor et al., "The production of monoclonal antibodies from human lymphocytes", Immunol Today, 4(3): 72-9 (1983).
Krause et al., "Antigen-dependent CD28 Signaling Selectively Enhances Survival and Proliferation in Genetically Modified Activated Human Primary T Lymphocytes", J. Exp. Med., 188(4): 619-626 (1998).
Lackie et al. (2013)The Dictionary of Cell and Molecular Biology, 5th edition, Academic Press, 748 pages.
Lamers et al., "Immune responses to transgene and retroviral vector in patients treated with ex vivo- engineered T cells," Blood, 117 (1), 72-82 (2011).
Larson et al., Pre-clinical development of gene modification of haematopoietic stem cells with chimeric antigen receptors for cancer immunotherapy, Human Vaccines & Immunotherapeutics 2017, vol. 13, No. 5, 1094-1104.
Latza et al., "The human OX40 homolog: cDNA structure, expression and chromosomal assignment of the ACT35 antigen," European Journal of Immunology, 24 (3), 677-683 (1994).
Lee et al. (2015), "T cells expressing CD19 chimeric antigen receptors for acute lymphoblastic leukaemia in children and young adults: a phase 1 dose-escalation trial", The Lancet, 385, 517-528.
Li et al., A good response of refractory mantel cell lymphoma to haploidentical Car T cell therapy after failure of autologous Car T cell therapy, Journal for ImmunoTherapy of Cancer 2019, vol. 7, No. 51. 7 pages.
Ling et al., "Advances in cancer immunotherapy based on chimeric antigen receptor," Translational Med. J., 4 (3), 97-104 (2015).
Lippow et al., "Computational design of antibody-affinity improvement beyond in vivo maturation," Nature Biotechnology, 25(10) pp. 1171-1176. (Year: 2007).
Littman et al., The isolation and sequence of the gene encoding T8: A molecule defining functional classes of T lymphocytes, Cell 1985, vol. 40, pp. 237-246.
Liu et al., Current approaches and advance in mantle cell lymphoma treatment, Stem Cell 2015, 2;18.
Lo et al., "Conformational epitope matching and prediction," BMC Genomics, 22(Suppl 2) pp. 1-16 (Year: 2021).
Lonberg et al. "Human antibodies from transgenic mice", Intern. Rev. Immunol., 13(1) 65-93 (1995).
Lonberg et al., "Antigen-specific human antibodies from mice comprising four distinct genetic modifications", Nature, 368(6474): 856-859 (1994).
Mangogna et al. Rituximab Plus Chemotherapy Provides No. Clinical Benefit in a Peripheral T-Cell Lymphoma not Otherwise Specified with Aberrant Expression of CD20 and CD79a: A Case Report and Review of the Literature. Diagnostics 10:341, 2020; doi:10.3390/diagnostics10060341.
Mannering et al., "A sensitive method for detecting proliferation of rare autoantigen-specific human T cells," Journal of Immunological Methods, 283 (1-2), 173-183 (2003).
Marks et al., "By-passing immunization. Human antibodies from V-gene libraries displayed on phage", J. Mol. Biol., 22(3):581-97 (1991).
Marks et al., "By-passing immunization: building high affinity human antibodies by chain shuffling", Biotechnology, 10(7):779-783 (1992).
Martin et al., "Postibrutinib outcomes in patients with mantle cell lymphoma", Clinical Trials and Observations, Blood, vol. 127, No. 12, Mar. 24, 2016, pp. 1559-1563.
Maude et al. (2018), "Tisagenlecleucel in Children and Young Adults with B-Cell Lymphoblastic Leukemia", The New England Journal of Medicine, 378(5), 439-448.
McPherson, Jr., "Crystallization of Proteins from Polyethylene Glycol", J Biol Chem, 251 (20): 6300-6303 (1976).
McPherson, "Current approaches to macromolecular crystallization", Eur J Biochem, 189: 1-23 (1990).
Moldenhauer et al., Identity of HML-1 Antigen on Intestinal Intraepithelial T Cells and of B-ly7 Antigen on Hairy Cell Leukaemia, Scandinavian Journal of Immunology, 32(2): 77-82 (1990).
Moran et al., "The TNFRs OX40, 4-1BB, and CD40 as targets for cancer immunotherapy," Current Opinion in Immunology, 25 (2), 230-237 (2013).
Morel et al., "Monoclonal antibodies to bovine serum albumin: affinity and specificity determinations", Mol Immunol, 25(1): 7-15 (1988).

(56) References Cited

OTHER PUBLICATIONS

Morrison, "Success in specification", Nature, 368, 812-13 (1994) 10.1038/368812a0.
Nadler et al., "B4, a human B lymphocyte-associated antigen expressed on normal, mitogen-activated, and malignant B lymphocytes," Journal of Immunology, 131 (1), 244-250 (1983).
Neelapu, 2-Year Follow-up and High-Risk Subset Analysis of Zuma-1, the Pivotal Study of Axicabtagene Ciloleucel (Axi-Cel) in Patients with Refractory Large B Cell Lymphoma Sattva S. Neelapu MD Abstracts / Biol Blood Marrow Transplant 25 (2019).
Neelapu et al. (2018), "Chimeric antigen receptor T-cell therapy - assessment and management of toxicities", Nature Reviews, Clinical Oncology, 15, 47-62.
Neelapu et al., "Kte-C19 (anti-CD19 Car T Cells) Induces Complete Remissions in Patients with Refractory Diffuse Large B-Cell Lymphoma (DLBCL): Results from the Pivotal Phase 2 Zuma-1," Blood, 2016, Abstract.
Neuberger, "Generating high-avidity human Mabs in mice", Nature Biotechnology, 14: 826 (1996).
Nguyen et al. (2008), "Factors influencing survival after relapse from acute lymphoblastic leukemia: a Children's Oncology Group study", Leukemia, 22, 2142-2150.
Nicholson et al., "Construction and characterisation of a functional CD19 specific single chain Fv fragment for immunotherapy of B lineage leukaemia and lymphoma," Molecular Immunology, 34 (16-17), 1157-1165 (1997).
Notice of Preliminary Rejection for Korean Application No. 10-2021-7021608 dated Oct. 20, 2024. 4 pages.
Notice of Preliminary Rejection for Korean Application No. 10-2021-7021608 dated Feb. 26, 2024. 6 pages.
Notice of Preliminary Rejection for Korean Application No. 10-2021-7021608 dated Aug. 18, 2023. 17 pages.
Ochi et al., "Functional immunoglobulin M production after transfection of cloned immunoglobulin heavy and light chain genes into lymphoid cells," Proceedings of the National Academy of Sciences of the United States of America, 80 (20), 6351-6355 (1983).
Office Action and Search Report for Taiwan Application No. 110125603 dated Oct. 31, 2023. 20 pages.
Office Action for Canadian Application No. 3,122,762 dated Nov. 4, 2024. 3 pages.
Office Action for Canadian Application No. 3,122,762 dated Sep. 18, 2023. 7 pages.
Office Action for Canadian Application No. 3,177,829 dated Feb. 23, 2024. 5 pages.
Office Action for Chinese Application No. 201980091506.9 dated Aug. 7, 2024. 15 pages.
Office Action for Chinese Application No. 201980091506.9 dated Mar. 18, 2024. 19 pages.
Office Action for Israeli Application No. 283734 dated Oct. 26, 2023. 5 pages.
Office Action for Japanese Application No. 2021-533159 dated Jan. 10, 2023. 4 pages.
Office Action for Japanese Application No. 2021-533159 dated Jul. 5, 2022. 10 pages.
Office Action, issued in TW Application No. 108145595, dated Jan. 13, 2021.
Oskarsson et al. (2016), "Relapsed childhood acute lymphoblastic leukemia in the Nordic countries: prognostic factors, treatment and outcome", Acute Lymphoblastic Leukemia, Haematologica, 101(1), 68-76.
Park et al. (2018), "Long-Term Follow-up of CD19 Car Therapy in Acute Lymphoblastic Leukemia", The New England Journal of Medicine, 449-459.
Partial Supplementary European Search Report for European Application No. 20886085.8 dated Apr. 5, 2024. 23 pages.
Patel et al., T-cell killing of heterogenous tumor or viral targets with bispecific chimeric immune receptors. Cancer Gene Therapy 2000, vol. 7, No. 8, pp. 1127-1134, XP055259929.
Pinchera et al. (eds.), "Analysis, Results, And Future Prospective Of The Therapeutic Use Of Radiolabeled Antibody In Cancer Therapy", in Monoclonal Antibodies For Cancer Detection And Therapy, pp. 475-506 (1985).
Porter et al., "Chimeric antigen receptor-modified T cells in chronic lymphoid leukemia", N. Engl. J. Med., 365(8):725-33 (2011).
Porter et al., "Comparison of efficiency of infection of human gene therapy target cells via four different retroviral receptors," Human Gene Therapy, 7 (8), 913-919 (1996).
Raboisson et al., Structure-activity relationship study on a novel series of cyclopentane-containing macrocyclic inhibitors of the hepatitis C virus NS3/4A protease leading to the discovery of TMC435350. Bioorganic & Medicinal Chemistry Letters 2008, vol. 18, No. 17, doi:10.1016/J.BMCL.2008.07.088, pp. 4853-4858, XP024100116.
Ramos et al., "CAR-T Cell Therapy for Lymphoma," Annu. Rev. Med. 67, pp. 165-183 (Year: 2016).
Ren et al., Multiplex Genome Editing to Generate Universal Car T Cells Resistant to PD1 Inhibition, Clin Cancer Res 2017; 23(9); 2255-2266.
Rheingold et al. (2019), "Prognostic factors for survival after relapsed acute lymphoblastic leukemia (All): A Children's Oncology Group (COG) study", Journal of Clinical Oncology, List of Issues, 37(15), 1-5.
Rosenberg et al., "Adoptive cell transfer as personalized immunotherapy for human cancer", Cancer Immunology and Immunotherapy, 348: 62-68 (2015).
Rubio et al., "Ex vivo identification, isolation and analysis of tumor-cytolytic T cells," Nature Medicine, 9 (11), 1377-1382 (2003).
Ruella et al., The Addition of the BTK Inhibitor Ibrutinib to Anti-CD19 Chimeric Antigen Receptor T Cells (CART19) Improves Responses against Mantle Cell Lymphoma, Clinical Cancer Research, 2016, 22(11):2684-2696.
Sabatino et al., "Production of Anti-CD19 Car T Cells for ZUMA-3 and -4: Phase 1/2 Multicenter Studies Evaluating KTE-C19 in Patients With Relapsed/Refractory B-Precursor Acute Lymphoblastic Leukemia (R/R All)", Blood, 128 (2), 1-6.
Sadelain et al., "Targeting Tumors with Genetically Enhanced T Lymphocytes", Nature Rev. Cancer, 3: 35-45 (2003).
Sadelain et al., CD19 Car Therapy for Acute Lymphoblastic Leukemia, American Society of Clinical Oncology Educational Book 2015, e360-e363.
Salles et al. Rituximab in B-Cell Hematologic Malignancies: A Review of 20 Years of Clinical Experience. Adv Ther 34: 2232-2273, 2017.
Savoldo et al., "CD28 costimulation improves expansion and persistence of chimeric antigen receptor-modified T cells in lymphoma patients," Journal of Clinical Investigation, 121 (5), 1822-1826 (2011).
Schneider et al., Minimizing leukemia escape: implementing a dual anti-CD20- and CD19-scFv-based chimeric antigen receptor (CAR). Journal for Immuno Therapy of Cancer 2015, vol. 3, No. 2, doi:10.1186/2051-1426-3-S2-P122, XP021235172. 1 page.
Schrappe et al. (2012), "Outcomes after Induction Failure in Childhood Acute Lymphoblastic Leukemia", The New England Journal of Medicine, 366(15), 1371-1381.
Schuster et al. (2019), "Tisagenlecleucel in Adult Relapsed or Refractory Diffuse Large B-Cell Lymphoma", The New England Journal of Medicine, 380(1), 45-56.
Schuster et al., "Chimeric Antigen Receptor T Cells in Refractory B-Cell Lymphomas," The New England Journal of Medicine, 2017, vol. 377, pp. 2545-2554.
Shah et al., "End of phase I results of ZUMA-3, a phase 1/2 study of KTE-X19, anti-CD19 chimeric antigen receptor (Car) T cell therapy, in adult patients (pts) with relapsed/refractory (R/R) acute lymphoblastic leukemia (ALL)," 2019, Meeting Abstract: 2019 ASCO Annual Meeting I, Journal of Clinical Oncology, vol. 37, No. 15 Supp., 3 pages.
Shah et al., A Phase 1 Study with Point-of-Care Manufacturing of Dual Targeted, Tandem Anti-CD19, Anti-CD20 Chimeric Antigen Receptor Modified T (Car-T) Cells for Relapsed, Refractory, Non-Hodgkin Lymphoma, Blood 2018, vol. 132, (Supplement 1): 4193, DOI: 10.1182/blood-2018-99-110194. 4 pages.

(56) References Cited

OTHER PUBLICATIONS

Shah, B et al., "High Rates of Minimal Residual Disease-Negative (MRD-) Complete Responses (CR) in Adult and Pediatric and Patients with Relapsed/Refractory Acute Lymphoblastic Leukemia (R/R All) Treated with KTE-C19 (anti-CD19 Chimeric Antigen Receptor [Car} T Cells): Preliminary Results of the ZUMA-3 and ZUMA-4 Trials", Blood, 128, Issue 22, p. 2803, http://doi.org/10.1182/blood.V128.22.2803.2803, Dec. 2, 2016 (Feb. 12, 2016).
Sommermeyer et al., Fully human CD19-specific chimeric antigen receptors for T-cell therapy, Leukemia 31(10): 2191-2199 (2017).
Song et al., "CD27 costimulation augments the survival and anti-tumor activity of redirected human T cells in vivo", Blood, 119(3): 696-706 (2012).
Sotillo et al. (2015), "Convergence of Acquired Mutations and Alternative Splicing of CD19 Enables Resistance to CART-19 Immunotherapy", Cancer Discovery, OF1-OF14.
Stackelberg et al. (2016), "Phase I/Phase II Study of Blinatumomab in Pediatric Patients With Relapsed/Refractory Acute Lymphoblastic Leukemia", Journal of Clinical Oncology, 34(36), 4381-4389.
Stahli et al., "Distinction of epitopes by monoclonal antibodies", Methods in Enzymology, 92: 242-253 (1983).
Sun et al. (2018), "Outcome of children with multiply relapsed B-cell acute lymphoblastic leukemia: a therapeutic advances in childhood leukemia & lymphoma study", Acute lymphoblastic leukemia, Springer Nature, 32, 2316-2325.
Swerdlow et al., "The 2016 revision of the World Health Organization classification of lymphoid neoplasms," Blood, 2016, vol. 127, No. 20, 16 pages.
Tammana et al., 4-1BB and CD28 Signaling Plays a Synergistic Role in Redirecting Umbilical Cord Blood T Cells Against B-Cell Malignancies, Human Gene Therapy 2010 , 21, pp. 75-86.
Thorpe et al., Monoclonal antibodies "84: biological and clinical applications : Proceedings of the International Symposium on Monoclonal antibodies "84 held in Florence, Italy, Oct. 16-19 (1984).
Thorpe et al., "The preparation and cytotoxic properties of antibody-toxin conjugates", Immunol. Rev., 62: 119-58 (1982).
Topp et al. (2014), "Safety and activity of blinatumomab for adult patients with relapsed or refractory B- precursor acute lymphoblastic leukaemia: a multicentre, single-arm, phase 2 study", The Lancet, 16, 57- 66.
Tramontano et al., "Framework residue 71 is a major determinant of the position and conformation of the second hypervariable region in the VH domains of immunoglobulins" J Mol Biol, 215(1):175-82 (1990).
Turtle et al., Immunotherapy of non-Hodgkin lymphoma with a defined ratio of CD8+ and CD4+ CD19-specific chimeric antigen receptor-modified T cells, Science Translational Medicine 2016, vol. 8, No. 355, doi:10.1126/scitranslmed.aaf8621. 24 pages.
UniprotKB-P01732 (CD8A Human) (12 pages) Jul. 21, 1986.
Urbanska et al., Targeted cancer immunotherapy via combination of designer bispecific antibody and novel gene-engineered T cells. Journal of Translational Medicine 2014, vol. 12, No. 1, XP021207565. 12 pages.
Venkatraman et al., Macrocyclic inhibitors of Hcv NS3 protease. Expert Opinion on Therapeutic Patents 2009, vol. 19, No. 9, doi: 10.1517/13543770903044994, pp. 1277-1303, XP055084885. https://doi.org/10.1517/13543770903044994.
Wang et al. (2017), "Acalabrutinib in relapsed or refractory mantle cell lymphoma (ACE-LY-004): a single-arm, multicentre, phase 2 trial", The Lancet, 1-9.
Wang et al. (2020), "KTE-X19 Car T-Cell Therapy in Relapsed or Refractory Mantle-Cell Lymphoma", The New England Journal of Medicine, 382(14), 1331-1342.
Wang et al., Safety and preliminary efficacy in patients (pts) with relapsed/refractory (R/R) mantle cell lymphoma (MCL) receiving lisocabtagene maraleucel (Liso-cel) in Transcend Nhl 001, Journal of Clinical Oncology, vol. 37, No. 15_suppl, May 26, 2019.
Wang et al., ZUMA-2: A phase 2 multi-center study evaluating the efficacy of KTE-C19 (Anti-CD19 Car T cells) in patients with relapsed/refractory mantle cell lymphoma (R/R MCL), Annals of Oncology, 2016, vol. 27(Supplement 6): vi326, doi:10.1093/annonc/mdw375.40. 2 pages.
Weinberg et al., "Science gone translational: the OX40 agonist story," Immunological Reviews, 244 (1), 218-231 (2011), Author Manuscript.
White et al. Cancer Prevention for the Next Generation. J Adolesc Health 52: S1-S7, 2013.
Wicks et al. (2015), "Targeting GM-CSF in inflammatory diseases", Nature Reviews, Rheumatology, 1-12.
Wong et al., "Ab-Ligity: identifying sequence-dissimilar antibodies that bind to the same epitope," MABS, vol. 13, No. 1 pp. 1-8 (Year: 2021).
Wu et al., "Remote control of therapeutic T cells through a small molecule-gated chimeric receptor", Science, 350:6258 (2014).
Yang et al., "A simplified method for the clinical-scale generation of central memory-like CDS+ T cells after transduction with lentiviral vectors encoding antitumor antigen T-cell receptors," Journal of Immunotherapy, 33 (6), 648-658 (2010).
Yoon-Hwan, "High-grade B-cell lymphoma," Korean Society for Laboratory Hematology News Letter, 2017, vol. 23, 3 pages.
Zebedee et al., "Human combinatorial antibody libraries to hepatitis B surface antigen", Proc. Natl. Acad. Sci. USA, 89(8): 3175-79 (1992).
Zhao et al. Universal CARs, universal T cells, and universal CART cells. J Hematol Oncol 11: 132, 2018, 9 pages.
Decision of Final Rejection for Japanese Application No. 2023-132752 dated Aug. 5, 2025, 4 pages.
"Hematopoietic and Lymphoid Tumors—WHO Classification, 2016 Version," Journal of Clinical Laboratory Medicine, vol. 61., No. 7, 2017, pp. 847-888.
Kochenderfer et al., Adoptive transfer of syngeneic T cells transduced with a chimeric antigen receptor that recognizes murine CD19 can eradicate lymphoma and normal B cells. Blood. Nov. 11, 2010;116(19):3875-86.
Penfold et al., "The FDA grants KTE-C19 Priority Review for the treatment of transplant-ineligible relapsed/refractory Non-Hodgkin Lymphoma," LymphomaHub, 2017, 1 page.
Gore L. et al. "Survival after blinatumomab treatment in pediatric patients with relapsed/refactory B-cell precursor acute lymphoblastic leukemia", Blood Cancer J. Aug. 22, 2018; 8(9):80. (Year 2018).
Kansagra Aj et al. "Clinical utilization of Chimeric Antigen Receptor T-cells (CAR-T) in B-cell acute lymphoblastic leukemia (ALL)—an expert opinion from the (EBMT) and the (ASBMT)", Bone Marrow Transplant. Nov. 2019; 54(11):1868-1880 (Year: 2019).
Paul S et al. "Adult-Acute Lymphoblastic Leukemia" Symposium on neoplastic hematology and medical oncology, vol. 91 Issue 11 p. 1645-1666 Nov. 2016 (Year 2016).
Schneider et al: "A tandem CD19/CD20 Car lentiviral vector drives on-target and off-target antigen modulation in leukemia cell lines", Journal for Immunotherapy of Cancer, Biomed Central Ltd, London, UK, vol. 5, No. 1, May 16, 2017 (May 16, 2017), pp. 1-17, XP021245145, DOI: 10.1186/S40425-017-0246-1.
Zah et al: "T Cells Expressing CD19/CD20 Bispecific Chimeric Antigen Receptors Prevent Antigen Escape by Malignant B Cells", Cancer Immunology Research, vol. 4, No. 6, Apr. 8, 2016 (Apr. 8, 2016), pp. 498-508, XP055290967, US ISSN: 2326-6066, DOI:10.1158/2326-6066.CIR-15-0231.

* cited by examiner

METHODS OF ADMINISTERING CHIMERIC ANTIGEN RECEPTOR IMMUNOTHERAPY

CROSS-REFERENCE TO RELATED APPLICATIONS

This application is a continuation of U.S. application Ser. No. 16/164,147, filed Oct. 18, 2018, which claims priority to U.S. Provisional Application No. 62/574,159, filed Oct. 18, 2017, the content of each of which is incorporated by reference herein in their entirety.

TECHNICAL FIELD

The present disclosure relates generally to T cell therapies and more specifically to CD19-directed genetically modified autologous T cell immunotherapies comprising chimeric antigen receptors (CARs).

BACKGROUND

Human cancers are by their nature comprised of normal cells that have undergone a genetic or epigenetic conversion to become abnormal cancer cells. In doing so, cancer cells begin to express proteins and other antigens that are distinct from those expressed by normal cells. These aberrant tumor antigens may be used by the body's innate immune system to specifically target and kill cancer cells. However, cancer cells employ various mechanisms to prevent immune cells, such as T and B lymphocytes, from successfully targeting cancer cells.

Chimeric antigen receptors (CARs), which comprise binding domains capable of interacting with a particular tumor antigen, allow T cells to target and kill cancer cells that express the particular tumor antigen.

SUMMARY

As described in detail below, the present disclosure is based, in part, on the surprising discovery that the administration methods disclosed herein identify and manage adverse side effects of CAR T-cell immunotherapy.

Any aspect or embodiment described herein may be combined with any other aspect or embodiment as disclosed herein. While the present invention has been described in conjunction with the detailed description thereof, the foregoing description is intended to illustrate and not limit the scope of the present invention, which is defined by the scope of the appended claims. Other aspects, advantages, and modifications are within the scope of the following claims.

In one aspect, the invention provides a method of treating relapsed or refractory diffuse large B-cell lymphoma (DLBCL) not otherwise specified, primary mediastinal large B-cell lymphoma, high grade B-cell lymphoma, or DLBCL arising from follicular lymphoma after two or more lines of systemic therapy in a patient comprising: administering to the patient in need thereof axicabtagene ciloleucel suspension by intravenous infusion at a dose between about $1\times10^6$ and about $2\times10^6$ CAR-positive viable T cells per kg body weight up to a maximum dose of about $1\times10^8$ CAR-positive viable T cells, wherein axicabtagene ciloleucel is a CD19-directed genetically modified autologous T cell immunotherapy, comprising the patient's own T cells harvested and genetically modified ex vivo by retroviral transduction to express a chimeric antigen receptor (CAR) comprising an anti-CD19 single chain variable fragment (scFv) linked to CD28 and CD3-zeta co-stimulatory domains.

In another aspect, the invention provides a method of treating relapsed or refractory diffuse large B-cell lymphoma (DLBCL) and primary mediastinal large B-cell lymphoma (PMBCL), after two or more lines of systemic therapy in a patient comprising: administering to the patient in need thereof axicabtagene ciloleucel suspension by intravenous infusion at a dose between about $0.4\times10^8$ and about $2\times10^8$ CAR-positive viable T cells, wherein axicabtagene ciloleucel is a CD19-directed genetically modified autologous T cell immunotherapy, comprising the patient's own T cells harvested and genetically modified ex vivo by retroviral transduction to express a chimeric antigen receptor (CAR) comprising an anti-CD19 single chain variable fragment (scFv) linked to CD28 and CD3-zeta co-stimulatory domains.

In some embodiments, the intravenous infusion time is between 15 and 120 minutes. In some embodiments, the intravenous infusion time is up to 30 minutes.

In some embodiments, the infusion volume is between 50 and 100 mL. In some embodiments, the infusion volume is about 68 mL.

In some embodiments, the immunotherapy is infused from an infusion bag. In some embodiments, the infusion bag is agitated during the infusion.

In some embodiments, the immunotherapy is administered within 3 hours after thawing.

In some embodiments, the suspension further comprises albumin. In some embodiments, albumin is present in an amount of about 2-3% (v/v). In some embodiments, albumin is present in an amount of about 2.5% (v/v). In some embodiments, albumin is human albumin.

In some embodiments, the suspension further comprises DMSO. In some embodiments, DMSO is present in an amount of about 4-6% (v/v). In some embodiments, DMSO is present in an amount of about 5% (v/v).

In one aspect, the invention provides a method of treating relapsed or refractory large B-cell lymphoma after two or more lines of systemic therapy in a patient comprising: (a) administering to the patient in need thereof CD19-directed genetically modified autologous T cell immunotherapy; and (b) monitoring the patient following infusion for signs and symptoms of an adverse reaction.

In some embodiments, the relapsed or refractory large B-cell lymphoma is diffuse large B-cell lymphoma (DLBCL) not otherwise specified, primary mediastinal large B-cell lymphoma, high grade B-cell lymphoma, or DLBCL arising from follicular lymphoma.

In some embodiments, the adverse reaction is selected from the group consisting of cytokine release syndrome (CRS), a neurologic toxicity, a hypersensitivity reaction, a serious infection, a cytopenia and hypogammaglobulinemia.

In some embodiments, the signs and symptoms of adverse reactions are selected from the group consisting of fever, hypotension, tachycardia, hypoxia, and chills, include cardiac arrhythmias (including atrial fibrillation and ventricular tachycardia), cardiac arrest, cardiac failure, renal insufficiency, capillary leak syndrome, hypotension, hypoxia, organ toxicity, hemophagocytic lymphohistiocytosis/macrophage activation syndrome (HLH/MAS), seizure, encephalopathy, headache, tremor, dizziness, aphasia, delirium, insomnia anxiety, anaphylaxis, febrile neutropenia, thrombocytopenia, neutropenia, and anemia.

In some embodiments, the method further comprises administering an IL-6 receptor inhibitor.

In some embodiments, the method further comprises administering an effective amount of tocilizumab to treat a symptom of an adverse reaction.

In some embodiments, tocilizumab is administered at a dose of about 8 mg/kg intravenously. In some embodiments, tocilizumab is administered intravenously over about 1 hour. In some embodiments, tocilizumab is administered about every 8 hours. In some embodiments, tocilizumab is administered for no more than about 24 hours.

In some embodiments, the method further comprises administering a corticosteroid to treat a symptom of an adverse reaction.

In some embodiments, the corticosteroid is at least one of methylprednisone or dexamethasone.

In some embodiments, methylprednisone is administered at a dose of about 1 mg/kg intravenously. In some embodiments, methylprednisone is administered twice daily. In some embodiments, methylprednisone is administered at a dose of about 1,000 mg per day intravenously. In some embodiments, methylprednisone is administered intravenously for about 3 days.

In some embodiments, dexamethasone is administered at a dose of about 10 mg. In some embodiments, dexamethasone is administered intravenously about every 6 hours.

In some embodiments, the adverse reaction is cytokine release syndrome (CRS). In some embodiments, the monitoring for signs and symptoms of cytokine release syndrome (CRS) is at least daily for about 7 days following infusion. In some embodiments, the monitoring for signs and symptoms of cytokine release syndrome (CRS) is at least daily for about 8 days, about 9 days, or about 10 days following infusion. In some embodiments, the monitoring for signs and symptoms of cytokine release syndrome (CRS) is at least daily for about 10 days following infusion. In some embodiments, the monitoring for signs and symptoms of cytokine release syndrome (CRS) is for about 4 weeks following infusion.

In some embodiments, the adverse reaction is neurologic toxicity.

In some embodiments, the monitoring for signs and symptoms of neurologic toxicity up to about 8 weeks following infusion.

In some embodiments, the method further comprises administering a non-sedating, anti-seizure medicine for seizure prophylaxis.

In some embodiments, the non-sedating, anti-seizure medicine is levetiracetam.

In some embodiments, the adverse reaction is a cytopenia. In some embodiments, the cytopenia is thrombocytopenia, neutropenia, and/or anemia.

In some embodiments, the method further comprises administering at least one of erythropoietin, darbepoetin alfa, platelet transfusion, colony-stimulating factor (CSF), granulocyte colony-stimulating factor, filgrastim, pegfilgrastim, or granulocyte-macrophage colony-stimulating factor.

In some embodiments, the method further comprises measuring cytokine and chemokine levels. In some embodiments, the level of at least one of IL-6, IL-8, IL-10, IL-15, TNF-α, IFN-γ, and sIL2Rα is measured.

In one aspect, the invention provides a container comprising a suspension of CD19-directed genetically modified autologous T cells, about 5% dimethylsulfoxide (DMSO) and about 2.5% human albumin (v/v). In another aspect, the container comprises a suspension of between about $0.4\times10^{8}$-$2\times10^{8}$ CD19-directed genetically modified autologous T cells (CAR-positive viable T cells).

In some embodiments, the container is a sterile infusion bag. In some embodiments, the infusion bag volume is about 100 mL, 250 mL, 500 mL, 750 mL, 1000 mL, 1500 mL, 2000 mL or 3000 mL.

In one aspect, the invention provides a method of treating relapsed or refractory large B-cell lymphoma after two or more lines of systemic therapy in a human comprising administering to the human in need thereof CD19-directed genetically modified autologous T cell immunotherapy comprising: (a) administering to the patient a composition comprising CD19-directed chimeric antigen receptor (CAR) positive viable T cells; (b) monitoring the patient following administration for signs and symptoms of an adverse reaction; and (c) if cytokine release syndrome (CRS) greater than Grade 2 is observed in (b), administering tocilizumab at a dose of about 8 mg/kg IV over 1 hour, repeating tocilizumab every 8 hours as needed if not responsive to IV fluids or increasing supplemental oxygen; (d) if CRS symptoms observed in (b) do not improve after 24 hours of (c), administering methylprednisolone about 1 mg/kg IV twice daily or administering equivalent dexamethasone dose and continuing corticosteroids use until the event is Grade 1 or less, then tapering over 3 days; (e) if CRS Grade 3 is observed in (b), administering tocilizumab at a dose of 8 mg/kg IV over 1 hour, repeating tocilizumab every 8 hours as needed if not responsive to IV fluids or increasing supplemental oxygen and administering methylprednisolone 1 mg/kg IV twice daily or administering equivalent dexamethasone dose and continuing corticosteroids use until the event is Grade 1 or less, then tapering over 3 days; and (f) if CRS Grade 4 is observed in (b), administering tocilizumab at a dose of about 8 mg/kg IV over 1 hour, repeating tocilizumab every 8 hours as needed if not responsive to IV fluids or increasing supplemental oxygen and administering about 1,000 mg IV methylprednisolone per day for 3 days.

In one aspect, the invention provide a method of treating relapsed or refractory large B-cell lymphoma after two or more lines of systemic therapy in a patient comprising administering to the patient in need thereof CD19-directed genetically modified autologous T cell immunotherapy comprising: (a) administering to the patient a composition comprising CD19-directed chimeric antigen receptor (CAR) positive viable T cells; (b) monitoring the patient following administration for signs and symptoms of an adverse reaction; and (c) if cytokine release syndrome (CRS) and/or neurologic toxicity is observed, managing cytokine release syndrome (CRS) and/or neurologic toxicity according to Table 1 and/or Table 2.

Other features and advantages of the disclosure will be apparent from the following Detailed Description, including the Examples, and the claims.

DETAILED DESCRIPTION

The present disclosure relates to engineered cells (e.g., T cells) comprising a CD19 CAR genetically modified autologous T cell immunotherapy indicated for the treatment of adult patients with relapsed or refractory large B-cell lymphoma after two or more lines of systemic therapy, including diffuse large B-cell lymphoma (DLBCL) not otherwise specified, primary mediastinal large B-cell lymphoma, high grade B-cell lymphoma, and DLBCL arising from follicular lymphoma. In some embodiments, the present disclosure provides methods of treatment using the engineered T cells for the treatment of a patient suffering from a cancer.

To prepare CD19-directed genetically modified autologous T cell immunotherapy, a patient's own T cells may be harvested and genetically modified ex vivo by retroviral transduction to express a chimeric antigen receptor (CAR) comprising a murine anti-CD19 single chain variable fragment (scFv) linked to CD28 and CD3-zeta co-stimulatory domains. In some embodiments, the CAR comprises a murine anti-CD19 single chain variable fragment (scFv) linked to 4-1BB and CD3-zeta co-stimulatory domain. The anti-CD19 CAR T cells may be expanded and infused back into the patient, where they may recognize and eliminate CD19-expressing target cells. YESCARTA® (Axi-cel™; axicabtagene ciloleucel) is an example of such CD19-directed genetically modified autologous T cell immunotherapy. See Kochenderfer, et al., (J Immunother 2009; 32:689 702). Additional CD19 directed CAR therapies include JCAR017, JCAR015, JCAR014, Kymriah (tisagenlecleucel). See Sadelain et al. Nature Rev. Cancer Vol. 3 (2003), Ruella et al., Curr Hematol Malig Rep., Springer, NY (2016) and Sadelain et al. Cancer Discovery (April 2013).

CD19-directed genetically modified autologous T cell immunotherapy may be prepared from the patient's peripheral blood mononuclear cells, which are typically obtained via a standard leukapheresis procedure. The mononuclear cells may be enriched for T cells and activated with anti-CD3 antibody in the presence of IL-2, then transduced with the replication incompetent retroviral vector containing the anti-CD19 CAR transgene. The transduced T cells may be expanded in cell culture, washed, formulated into a suspension, and/or cryopreserved. Typically, the product comprising genetically modified autologous T cells must pass a sterility test before release for shipping as a frozen suspension in a patient-specific infusion container such as an infusion bag. Typically, the product is thawed prior to infusion.

In addition to T cells, CD19-directed genetically modified autologous T cell immunotherapy may contain NK and NK-T cells. In some embodiments, the CD19-directed genetically modified autologous T cell immunotherapy formulation contains about 5% dimethylsulfoxide (DMSO) and about 2.5% albumin (human) (v/v).

CD19-directed genetically modified autologous T cells bind to CD19-expressing cancer cells and normal B cells. Studies have demonstrated that, following anti-CD19 CAR T cell engagement with CD19-expressing target cells, the CD28 and CD3-zeta co-stimulatory domains activate downstream signaling cascades that lead to T-cell activation, proliferation, acquisition of effector functions and secretion of inflammatory cytokines and chemokines. This sequence of events leads to killing of CD19-expressing cells.

In one aspect, the invention provides a method of treating relapsed or refractory diffuse large B-cell lymphoma (DLBCL) not otherwise specified, primary mediastinal large B-cell lymphoma, high grade B-cell lymphoma, or DLBCL arising from follicular lymphoma after two or more lines of systemic therapy in a patient comprising: administering to the patient in need thereof a CD19-directed genetically modified autologous T cell suspension by intravenous infusion at a dose between about $1\times10^6$ and about $2\times10^6$ CAR-positive viable T cells per kg body weight up to a maximum dose of about $1\times10^8$ CAR-positive viable T cells.

Definitions

In order for the present invention to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The term "and/or" where used herein is to be taken as specific disclosure of each of the two specified features or components with or without the other. Thus, the term "and/or" as used in a phrase such as "A and/or B" herein is intended to include A and B; A or B; A (alone); and B (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The terms "e.g.," and "i.e." as used herein, are used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. It is understood that wherever aspects are described herein with the language "comprising," otherwise analogous aspects described in terms of "consisting of" and/or "consisting essentially of" are also provided.

Unless specifically stated or evident from context, as used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "approximately" may mean within one or more than one standard deviation per the practice in the art. "About" or "approximately" may mean a range of up to 10% (i.e., ±10%). Thus, "about" may be understood to be within 10%, 9%, 8%, 7%, 6%, 5% 4%, 3%, 2%, 1%, 0.5%, 0.1%, 0.05%, 0.01%, or 0.001% greater or less than the stated value. For example, about 5 mg may include any amount between 4.5 mg and 5.5 mg. Furthermore, particularly with respect to biological systems or processes, the terms may mean up to an order of magnitude or up to 5-fold of a value. When particular values or compositions are provided in the instant disclosure, unless otherwise stated, the meaning of "about" or "approximately" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

Units, prefixes, and symbols used herein are provided using their Système International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, "The Concise Dictionary of Biomedicine and Molecular Biology", 2nd ed., (2001), CRC Press; "The Dictionary of Cell & Molecular Biology", 5th ed., (2013), Academic Press; and "The Oxford Dictionary Of Biochemistry And Molecular Biology", Cammack et al. eds., 2nd ed, (2006), Oxford University Press, provide those of skill in the art with a general dictionary for many of the terms used in this disclosure.

"Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering may also be performed, for example, once, a plurality of times, and/or over one or more extended periods.

The term "antibody" (Ab) includes, without limitation, a glycoprotein immunoglobulin which binds specifically to an antigen. In general, and antibody may comprise at least two heavy (H) chains and two light (L) chains interconnected by disulfide bonds, or an antigen-binding molecule thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region is comprises one constant domain, CL. The VH and VL regions may be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (C1q) of the classical complement system.

Antibodies may include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')2 fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen-binding fragments of any of the above. In some embodiments, antibodies described herein refer to polyclonal antibody populations.

An "antigen binding molecule," "antigen binding portion," or "antibody fragment" refers to any molecule that comprises the antigen binding parts (e.g., CDRs) of the antibody from which the molecule is derived. An antigen binding molecule may include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In some embodiments, the antigen binding molecule binds to CD19. In further embodiments, the antigen binding molecule is an antibody fragment that specifically binds to the antigen, including one or more of the complementarity determining regions (CDRs) thereof. In further embodiments, the antigen binding molecule is a single chain variable fragment (scFv). In some embodiments, the antigen binding molecule comprises or consists of avimers.

An "antigen" refers to any molecule that provokes an immune response or is capable of being bound by an antibody or an antigen binding molecule. The immune response may involve either antibody production, or the activation of specific immunologically-competent cells, or both. A person of skill in the art would readily understand that any macromolecule, including virtually all proteins or peptides, may serve as an antigen. An antigen may be endogenously expressed, i.e. expressed by genomic DNA, or may be recombinantly expressed. An antigen may be specific to a certain tissue, such as a cancer cell, or it may be broadly expressed. In addition, fragments of larger molecules may act as antigens. In some embodiments, antigens are tumor antigens.

"CD19-directed genetically modified autologous T cell immunotherapy" refers to a suspension of chimeric antigen receptor (CAR)-positive T cells. An example of such immunotherapy is axicabtagene ciloleucel (also known as Axi-cel™, YESCARTA®), developed by Kite Pharmaceuticals, Inc.

The term "neutralizing" refers to an antigen binding molecule, scFv, antibody, or a fragment thereof, that binds to a ligand and prevents or reduces the biological effect of that ligand. In some embodiments, the antigen binding molecule, scFv, antibody, or a fragment thereof, directly blocking a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

The term "autologous" refers to any material derived from the same individual to which it is later to be re-introduced. For example, the engineered autologous cell therapy (eACT™) method described herein involves collection of lymphocytes from a patient, which are then engineered to express, e.g., a CAR construct, and then administered back to the same patient.

The term "allogeneic" refers to any material derived from one individual which is then introduced to another individual of the same species, e.g., allogeneic T cell transplantation.

The terms "transduction" and "transduced" refer to the process whereby foreign DNA is introduced into a cell via viral vector (see Jones et al., "Genetics: principles and analysis," Boston: Jones & Bartlett Publ. (1998)). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" may include a tumor. Examples of cancers that may be treated by the methods disclosed herein include, but are not limited to, cancers of the immune system including lymphoma, leukemia, myeloma, and other leukocyte malignancies. In some embodiments, the methods disclosed herein may be used to reduce the tumor size of a tumor derived from, for example, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T cell lymphoma, environmentally induced cancers including those induced by asbestos, other B cell malignancies, and combinations of said cancers. In some embodiments, the cancer is multiple myeloma. The particular cancer may be responsive to chemo- or radiation therapy or the cancer may be refractory. A refractor cancer refers to a cancer that is not amendable to surgical intervention and the cancer is either initially unresponsive to chemo- or radiation therapy or the cancer becomes unresponsive over time.

An "anti-tumor effect" as used herein, refers to a biological effect that may present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect may also refer to the prevention of the occurrence of a tumor, e.g., a vaccine.

A "cytokine," as used herein, refers to a non-antibody protein that is released by one cell in response to contact with a specific antigen, wherein the cytokine interacts with a second cell to mediate a response in the second cell. "Cytokine" as used herein is meant to refer to proteins released by one cell population that act on another cell as intercellular mediators. A cytokine may be endogenously expressed by a cell or administered to a subject. Cytokines may be released by immune cells, including macrophages, B cells, T cells, and mast cells to propagate an immune response. Cytokines may induce various responses in the recipient cell. Cytokines may include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines may promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perform. Examples of acute phase-proteins include, but are not limited to, C-reactive protein (CRP) and serum amyloid A (SAA).

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1a), MIP-1β (MIP-1b), gamma-induced protein 10 (IP-10), and thymus and activation regulated chemokine (TARC or CCL17).

A "therapeutically effective amount," "effective dose," "effective amount," or "therapeutically effective dosage" of a therapeutic agent, e.g., engineered CAR T cells, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression may be evaluated using a variety of methods known to the skilled practitioner, such as in human subjects during clinical trials, in animal model systems predictive of efficacy in humans, or by assaying the activity of the agent in in vitro assays.

The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T cells play a major role in cell-mediated-immunity (no antibody involvement). Its T cell receptors (TCR) differentiate themselves from other lymphocyte types. The thymus, a specialized organ of the immune system, is primarily responsible for the T cell's maturation. There are six types of T cells, namely: Helper T cells (e.g., CD4+ cells), Cytotoxic T cells (also known as TC, cytotoxic T lymphocyte, CTL, T-killer cell, cytolytic T cell, CD8+ T cells or killer T cell), Memory T cells ((i) stem memory TSCM cells, like naive cells, are CD45RO−, CCR7+, CD45RA+, CD62L+(L-selectin), CD27+, CD28+ and IL-7Rα+, but they also express large amounts of CD95, IL-2Rβ, CXCR3, and LFA-1, and show numerous functional attributes distinctive of memory cells); (ii) central memory TCM cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T cells (Tregs, suppressor T cells, or CD4+CD25+ regulatory T cells), Natural Killer T cells (NKT) and Gamma Delta T cells. B-cells, on the other hand, play a principal role in humoral immunity (with antibody involvement). It makes antibodies and antigens and performs the role of antigen-presenting cells (APCs) and turns into memory B-cells after activation by antigen interaction. In mammals, immature B-cells are formed in the bone marrow, where its name is derived from.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which may either be obtained from a patient or a donor. The cell may be modified to express an exogenous construct, such as, e.g., a chimeric antigen receptor (CAR) or a T cell receptor (TCR), which is incorporated into the cell's genome.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy may include adoptive T cell therapy, tumor-infiltrating lymphocyte (TIL) immunotherapy, autologous cell therapy, engineered autologous cell therapy (eACT™), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. Nos. 7,741,465, 6,319,494, 5,728,388, and International Publication No. WO 2008/081035.

The T cells of the immunotherapy may come from any source known in the art. For example, T cells may be differentiated in vitro from a hematopoietic stem cell population, or T cells may be obtained from a subject. T cells may be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells may be derived from one or more T cell lines available in the art. T cells may also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

The term "engineered Autologous Cell Therapy," which may be abbreviated as "eACT™," also known as adoptive cell transfer, is a process by which a patient's own T cells are collected and subsequently genetically altered to recognize and target one or more antigens expressed on the cell surface of one or more specific tumor cells or malignancies. T cells may be engineered to express, for example, chimeric antigen receptors (CAR). CAR positive (+) T cells are engineered to express an extracellular single chain variable fragment (scFv) with specificity for a particular tumor antigen linked to an intracellular signaling part comprising at least one costimulatory domain and at least one activating domain. The CAR scFv may be designed to target, for example, CD19, which is a transmembrane protein expressed by cells in the B cell lineage, including all normal B cells and B cell malignances, including but not limited to diffuse large B-cell lymphoma (DLBCL) not otherwise specified, primary mediastinal large B-cell lymphoma, high grade B-cell lymphoma, and DLBCL arising from follicular lymphoma, NHL, CLL, and non-T cell ALL. Example CAR T cell therapies and constructs are described in U.S. Patent Publication Nos. 2013/0287748, 2014/0227237, 2014/0099309, and 2014/0050708, and these references are incorporated by reference in their entirety.

A "patient" as used herein includes any human who is afflicted with a cancer (e.g., a lymphoma or a leukemia). The terms "subject" and "patient" are used interchangeably herein.

As used herein, the term "in vitro cell" refers to any cell which is cultured ex vivo. In particular, an in vitro cell may include a T cell.

The terms "peptide," "polypeptide," and "protein" are used interchangeably, and refer to a compound comprised of amino acid residues covalently linked by peptide bonds. A protein or peptide contains at least two amino acids, and no limitation is placed on the maximum number of amino acids that may comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Stimulation," as used herein, refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex, that specifically binds with a cognate stimulatory ligand present on an antigen present cell. A "stimulatory ligand" is a ligand that when present on an antigen presenting cell (e.g., an APC, a dendritic cell, a B-cell, and the like) may specifically bind with a stimulatory molecule on a T cell, thereby mediating a primary response by the T cell, including, but not limited to, activation, initiation of an immune response, proliferation, and the like. Stimulatory ligands include, but are not limited to, an anti-CD3 antibody, an MHC Class I molecule loaded with a peptide, a superagonist anti-CD2 antibody, and a superagonist anti-CD28 antibody.

A "costimulatory signal," as used herein, refers to a signal, which in combination with a primary signal, such as TCR/CD3 ligation, leads to a T cell response, such as, but not limited to, proliferation and/or upregulation or down regulation of key molecules.

A "costimulatory ligand," as used herein, includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand may include, but is not limited to, 3/TR6, 4-1BB ligand, agonist or antibody that binds Toll ligand receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MHC class I chain-related protein B (MICB), OX40 ligand, PD-L2, or programmed death (PD) L1. A co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD 33, CD 45, CD100 (SEMA4D), CD103, CD134, CD137, CD154, CD16, CD160 (BY55), CD18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CDl-1a, CDl-1b, CDl-1c, CDl-1d, CDS, CEACAM1, CRT AM, DAP-10, DNAM1 (CD226), Fc gamma receptor, GADS, GITR, HVEM (LIGHTR), IA4, ICAM-1, ICAM-1, ICOS, Ig alpha (CD79a), IL2R beta, IL2R gamma, IL7R alpha, integrin, ITGA4, ITGA4, ITGA6, ITGAD, ITGAE, ITGAL, ITGAM, ITGAX, ITGB2, ITGB7, ITGBl, KIRDS2, LAT, LFA-1, LFA-1, LIGHT, LIGHT (tumor necrosis factor superfamily member 14; TNFSF14), LTBR, Ly9 (CD229), lymphocyte function-associated antigen-1 (LFA-1 (CDl 1a/CD18), MHC class I molecule, NKG2C, NKG2D, NKp30, NKp44, NKp46, NKp80 (KLRF1), OX40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Lyl08), SLAMF7, SLP-76, TNF, TNFr, TNFR2, Toll ligand receptor, TRANCE/RANKL, VLA1, or VLA-6, or fragments, truncations, or combinations thereof.

The terms "reducing" and "decreasing" are used interchangeably herein and indicate any change that is less than the original. "Reducing" and "decreasing" are relative terms, requiring a comparison between pre- and post-measurements. "Reducing" and "decreasing" include complete depletions.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In some embodiments, "treatment" or "treating" includes a partial remission. In another embodiment, "treatment" or "treating" includes a complete remission.

Various aspects of the disclosure are described in further detail in the following subsections.

Chimeric Antigen Receptors

Chimeric antigen receptors (CARs or CAR-Ts) are genetically engineered receptors. These engineered receptors may be readily inserted into and expressed by immune cells, including T cells in accordance with techniques known in the art. With a CAR, a single receptor may be programmed to both recognize a specific antigen and, when bound to that antigen, activate the immune cell to attack and destroy the cell bearing that antigen. When these antigens exist on tumor cells, an immune cell that expresses the CAR may target and kill the tumor cell.

Engineered T Cells and Use

A CD19-directed genetically modified autologous T cell immunotherapy indicated for the treatment of patients with relapsed or refractory large B-cell lymphoma after two or more lines of systemic therapy, including diffuse large B-cell lymphoma (DLBCL) not otherwise specified, primary mediastinal large B-cell lymphoma, high grade B-cell lymphoma, and DLBCL arising from follicular lymphoma. In some embodiments, the CD19-directed genetically modified autologous T cell immunotherapy is axicabtagene ciloleucel (Axi-cel™, YESCARTA®).

The cell of the present disclosure may be obtained through T cells obtained from a subject. T cells may be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells may be derived from one or more T cell lines available in the art. T cells may also be obtained from a unit of blood collected from a subject using any number of techniques known to the skilled artisan, such as FICOLL™ separation and/or apheresis. In some embodiments, the cells collected by apheresis are washed to remove the plasma fraction, and placed in an appropriate buffer or media for subsequent processing. In some embodiments, the cells are washed with PBS. As will be appreciated, a washing step may be used, such as by using a semiautomated flow through centrifuge, e.g., the Cobe™ 2991 cell processor, the Baxter CytoMate™, or the like. In some embodiments, the washed cells are resuspended in one or more biocompatible buffers, or other saline solution with or without buffer. In some embodiments, the undesired components of the apheresis sample are removed. Additional methods of isolating T cells for a T cell therapy are disclosed in U.S. Patent Pub. No. 2013/0287748, which is herein incorporated by references in its entirety.

In some embodiments, T cells are isolated from PBMCs by lysing the red blood cells and depleting the monocytes, e.g., by using centrifugation through a PERCOLLT™ gradient. In some embodiments, a specific subpopulation of T cells, such as CD4+, CD8+, CD28+, CD45RA+, and CD45RO+ T cells is further isolated by positive or negative selection techniques known in the art. For example, enrichment of a T cell population by negative selection may be accomplished with a combination of antibodies directed to surface markers unique to the negatively selected cells. In some embodiments, cell sorting and/or selection via negative magnetic immunoadherence or flow cytometry that uses a cocktail of monoclonal antibodies directed to cell surface markers present on the cells negatively selected may be used. For example, to enrich for CD4+ cells by negative selection, a monoclonal antibody cocktail typically includes antibodies to CD8, CD11b, CD14, CD16, CD20, and HLA-DR. In some embodiments, flow cytometry and cell sorting are used to isolate cell populations of interest for use in the present disclosure.

In some embodiments, PBMCs are used directly for genetic modification with the immune cells (such as CARs) using methods as described herein. In some embodiments, after isolating the PBMCs, T lymphocytes are further isolated, and both cytotoxic and helper T lymphocytes are sorted into naive, memory, and effector T cell subpopulations either before or after genetic modification and/or expansion.

In some embodiments, CD8+ cells are further sorted into naive, central memory, and effector cells by identifying cell surface antigens that are associated with each of these types of CD8+ cells. In some embodiments, the expression of phenotypic markers of central memory T cells includes CCR7, CD3, CD28, CD45RO, CD62L, and CD127 and are negative for granzyme B. In some embodiments, central memory T cells are CD8+, CD45RO+, and CD62L+ T cells. In some embodiments, effector T cells are negative for CCR7, CD28, CD62L, and CD127 and positive for granzyme B and perforin. In some embodiments, CD4+ T cells are further sorted into subpopulations. For example, CD4+T helper cells may be sorted into naive, central memory, and effector cells by identifying cell populations that have cell surface antigens.

In some embodiments, the immune cells, e.g., T cells, are genetically modified following isolation using known methods, or the immune cells are activated and expanded (or differentiated in the case of progenitors) in vitro prior to being genetically modified. In another embodiment, the immune cells, e.g., T cells, are genetically modified with the chimeric antigen receptors described herein (e.g., transduced with a viral vector comprising one or more nucleotide sequences encoding a CAR) and then are activated and/or expanded in vitro. Methods for activating and expanding T cells are known in the art and are described, e.g., in U.S. Pat. Nos. 6,905,874; 6,867,041; and 6,797,514; and PCT Publication No. WO 2012/079000, the contents of which are hereby incorporated by reference in their entirety. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is The Dynabeads® system, a CD3/CD28 activator/stimulator system for physiological activation of human T cells. In other embodiments, the T cells are activated and stimulated to proliferate with feeder cells and appropriate antibodies and cytokines using methods such as those described in U.S. Pat. Nos. 6,040,177 and 5,827,642 and PCT Publication No. WO 2012/129514, the contents of which are hereby incorporated by reference in their entirety.

In some embodiments, the T cells are obtained from a donor subject. In some embodiments, the donor subject is human patient afflicted with a cancer or a tumor. In some embodiments, the donor subject is a human patient not afflicted with a cancer or a tumor.

In some embodiments, the composition comprises a pharmaceutically acceptable carrier, diluent, solubilizer, emulsifier, preservative and/or adjuvant. In some embodiments, the composition comprises an excipient.

In some embodiments, the composition is selected for parenteral delivery, for inhalation, or for delivery through the digestive tract, such as orally. The preparation of such pharmaceutically acceptable compositions is within the ability of one skilled in the art. In some embodiments, buffers are used to maintain the composition at physiological pH or at a slightly lower pH, typically within a pH range of from about 5 to about 8. In some embodiments, when parenteral administration is contemplated, the composition is in the form of a pyrogen-free, parenterally acceptable aqueous solution comprising a composition described herein, with or without additional therapeutic agents, in a pharmaceutically acceptable vehicle. In some embodiments, the vehicle for parenteral injection is sterile distilled water in which composition described herein, with or without at least one additional therapeutic agent, is formulated as a sterile, isotonic solution, properly preserved. In some embodiments, the preparation involves the formulation of the desired molecule with polymeric compounds (such as polylactic acid or polyglycolic acid), beads or liposomes, that provide for the controlled or sustained release of the product, which are then be delivered via a depot injection. In some embodiments, implantable drug delivery devices are used to introduce the desired molecule.

In some embodiments, the methods of treating a cancer in a subject in need thereof comprise a T cell therapy. In some embodiments, the T cell therapy disclosed herein is engineered Autologous Cell Therapy (eACT™). According to this embodiment, the method may include collecting blood cells from the patient. The isolated blood cells (e.g., T cells) may then be engineered to express a CAR or a TCR disclosed herein. In a particular embodiment, the CAR T cells or the TCR T cells are administered to the patient. In some embodiments, the CAR T cells or the TCR T cells treat a tumor or a cancer in the patient. In some embodiments the CAR T cells or the TCR T cells reduce the size of a tumor or a cancer.

In some embodiments, the donor T cells for use in the T cell therapy are obtained from the patient (e.g., for an autologous T cell therapy). In other embodiments, the donor T cells for use in the T cell therapy are obtained from a subject that is not the patient. The T cells may be administered at a therapeutically effective amount. For example, a therapeutically effective amount of the T cells may be at least about $10^4$ cells, at least about $10^5$ cells, at least about $10^6$ cells, at least about $10^7$ cells, at least about $10^8$ cells, at least about $10^9$, or at least about $10^{10}$. In another embodiment, the therapeutically effective amount of the T cells is about $10^4$ cells, about $10^5$ cells, about $10^6$ cells, about $10^7$ cells, or about $10^8$ cells. In some embodiments, the therapeutically effective amount of the CAR T cells is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg. In some embodiments, the therapeutically effective amount of the CAR-positive viable T cells is between about $1\times10^6$ and about $2\times10^6$ CAR-positive viable T cells per kg body weight up to a maximum dose of about $1\times10^8$ CAR-positive viable T cells.

In some embodiments, the therapeutically effective amount of the CAR-positive viable T cells is between about $0.4\times10^8$ and about $2\times10^8$ CAR-positive viable T cells. In some embodiments, the therapeutically effective amount of the CAR-positive viable T cells is about $0.4\times10^8$, about $0.5\times10^8$, about $0.6\times10^8$, about $0.7\times10^8$, about $0.8\times10^8$, about $0.9\times10^8$, about $1.0\times10^8$, about $1.1\times10^8$, about $1.2\times10^8$, about $1.3\times10^8$, about $1.4\times10^8$, about $1.5\times10^8$, about $1.6\times10^8$, about $1.7\times10^8$, about $1.8\times10^8$, about $1.9\times10^8$, or about $2.0\times10^8$ CAR-positive viable T cells.

Methods of Treatment

The methods disclosed herein may be used to treat a cancer in a subject, reduce the size of a tumor, kill tumor cells, prevent tumor cell proliferation, prevent growth of a tumor, eliminate a tumor from a patient, prevent relapse of a tumor, prevent tumor metastasis, induce remission in a patient, or any combination thereof. In some embodiments, the methods induce a complete response. In other embodiments, the methods induce a partial response.

Cancers that may be treated include tumors that are not vascularized, not yet substantially vascularized, or vascularized. The cancer may also include solid or non-solid tumors. In some embodiments, the cancer is a hematologic cancer. In some embodiments, the cancer is of the white blood cells. In other embodiments, the cancer is of the plasma cells. In some embodiments, the cancer is leukemia, lymphoma, or myeloma. In some embodiments, the cancer is acute lymphoblastic leukemia (ALL) (including non T cell ALL), acute lymphoid leukemia (ALL), and hemophagocytic lymphohistocytosis (HLH)), B cell prolymphocytic leukemia, B-cell acute lymphoid leukemia ("BALL"), blastic plasmacytoid dendritic cell neoplasm, Burkitt's lymphoma, chronic lymphocytic leukemia (CLL), chronic myelogenous leukemia (CML), chronic myeloid leukemia (CML), chronic or acute granulomatous disease, chronic or acute leukemia, diffuse large B cell lymphoma, diffuse large B cell lymphoma (DLBCL), follicular lymphoma, follicular lymphoma (FL), hairy cell leukemia, hemophagocytic syndrome (Macrophage Activating Syndrome (MAS), Hodgkin's Disease, large cell granuloma, leukocyte adhesion deficiency, malignant lymphoproliferative conditions, MALT lymphoma, mantle cell lymphoma, Marginal zone lymphoma, monoclonal gammapathy of undetermined significance (MGUS), multiple myeloma, myelodysplasia and myelodysplastic syndrome (MDS), myeloid diseases including but not limited to acute myeloid leukemia (AML), non-Hodgkin's lymphoma (NHL), plasma cell proliferative disorders (e.g., asymptomatic myeloma (smoldering multiple myeloma or indolent myeloma), plasmablastic lymphoma, plasmacytoid dendritic cell neoplasm, plasmacytomas (e.g., plasma cell dyscrasia; solitary myeloma; solitary plasmacytoma; extramedullary plasmacytoma; and multiple plasmacytoma), POEMS syndrome (Crow-Fukase syndrome; Takatsuki disease; PEP syndrome), primary mediastinal large B cell lymphoma (PMBC), small cell- or a large cell-follicular lymphoma, splenic marginal zone lymphoma (SMZL), systemic amyloid light chain amyloidosis, T cell acute lymphoid leukemia ("TALL"), T cell lymphoma, transformed follicular lymphoma, Waldenstrom macroglobulinemia, or a combination thereof.

In some embodiments, the cancer is a myeloma. In some embodiments, the cancer is multiple myeloma. In some embodiments, the cancer is a leukemia. In some embodiments, the cancer is acute myeloid leukemia.

In some embodiments, the methods further comprise administering a chemotherapeutic. In some embodiments, the chemotherapeutic selected is a lymphodepleting (preconditioning) chemotherapeutic. Beneficial preconditioning treatment regimens, along with correlative beneficial biomarkers are described in U.S. Provisional Patent Applications 62/262,143 and 62/167,750 which are hereby incorporated by reference in their entirety herein. These describe, e.g., methods of conditioning a patient in need of a T cell therapy comprising administering to the patient specified beneficial doses of cyclophosphamide (between 200 mg/m$^2$/day and 2000 mg/m$^2$/day) and specified doses of fludarabine (between 20 mg/m$^2$/day and 900 mg/m$^2$/day). One such dose regimen involves treating a patient comprising administering daily to the patient about 500 mg/m$^2$/day of cyclophosphamide and about 60 mg/m$^2$/day of fludarabine for three days prior to administration of a therapeutically effective amount of engineered T cells to the patient.

In some embodiments, the antigen binding molecule, transduced (or otherwise engineered) cells (such as CARs), and the chemotherapeutic agent are administered each in an amount effective to treat the disease or condition in the subject.

In some embodiments, compositions comprising CAR-expressing immune effector cells disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS2000; difluoromethylomithine (DMFO); retinoic acid derivatives such as Targretin™ (bexarotene), Panretin™, (alitretinoin); ONTAK™ (denileukin diftitox); esperamicins; capecitabine; and pharmaceutically acceptable salts, acids or derivatives of any of the above. In some embodiments, compositions comprising CAR- and/or TCR-expressing immune effector cells disclosed herein may be administered in conjunction with an anti-hormonal agent that acts to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®), Doxorubicin (hydroxydoxorubicin), Vincristine (Oncovin®), and Prednisone.

In some embodiments, the chemotherapeutic agent is administered at the same time or within one week after the administration of the engineered cell or nucleic acid. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell or nucleic acid. In some embodiments, the chemotherapeutic agent is administered at least 1 month before administering the cell or nucleic acid. In some embodiments, the methods further comprise administering two or more chemotherapeutic agents.

A variety of additional therapeutic agents may be used in conjunction with the compositions described herein. For example, potentially useful additional therapeutic agents include PD-1 inhibitors such as nivolumab (OPDIVO®), pembrolizumab (KEYTRUDA®), pembrolizumab, pidilizumab (CureTech), and atezolizumab (Roche).

Additional therapeutic agents suitable for use in combination with the compositions and methods disclosed herein include, but are not limited to, ibrutinib (IMBRUVICA®), ofatumumab (ARZERRA®), rituximab (RITUXAN®), bevacizumab (AVASTIN®), trastuzumab (HERCEPTIN®), trastuzumab emtansine (KADCYLA®), imatinib (GLEEVEC®), cetuximab (ERBITUX®), panitumumab (VECTIBIX®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib).

In some embodiments, the composition comprising CAR immune cells are administered with an anti-inflammatory agent. Anti-inflammatory agents or drugs may include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), non-steroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular), and minocycline.

In some embodiments, the compositions described herein are administered in conjunction with a cytokine. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO, Epogen®, Procrit®); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

Administration of CD19-Directed Genetically Modified Autologous T Cell Immunotherapy Indications and Usage In some embodiments, CD19-directed genetically modified autologous T cell immunotherapy indicated for the treatment of adult patients with relapsed or refractory large B-cell lymphoma after two or more lines of systemic therapy, including diffuse large B-cell lymphoma (DLBCL) not otherwise specified, primary mediastinal large B-cell lymphoma, high grade B-cell lymphoma, and DLBCL arising from follicular lymphoma. In some embodiments, CD19-directed genetically modified autologous T cell immunotherapy is not indicated for the treatment of patients with primary central nervous system lymphoma.

Dosage and Administration

In some embodiments, an infusion bag of CD19-directed genetically modified autologous T cell immunotherapy comprises a suspension of chimeric antigen receptor (CAR)-positive T cells in approximately 68 mL. The target dose may be between about $1\times10^6$ and about $2\times10^6$ CAR-positive viable T cells per kg body weight, with a maximum of $2\times10^8$ CAR-positive viable T cells. In some embodiments the CD19-directed genetically modified autologous T cell immunotherapy is Axi-cel™ (YESCARTA®, axicabtagene ciloleucel).

CD19-directed genetically modified autologous T cell immunotherapy is for autologous use. The patient's identity must match the patient identifiers on the CD19-directed genetically modified autologous T cell immunotherapy cassette and infusion bag. If the information on the patient-specific label does not match the intended patient, the CD19-directed genetically modified autologous T cell immunotherapy cannot be administered.

In some embodiments, the availability of CD19-directed genetically modified autologous T cell immunotherapy must be confirmed prior to starting the lymphodepleting regimen.

In some embodiments, the patient is pre-treated prior to CD19-directed genetically modified autologous T cell immunotherapy infusion with administration of lymphodepleting chemotherapy. In some embodiments, a lymphodepleting chemotherapy regimen of cyclophosphamide 500 mg/m$^2$ IV and fludarabine 30 mg/m$^2$ IV on the fifth, fourth, and third day before infusion of CD19-directed genetically modified autologous T cell immunotherapy is administered.

In some embodiments, the patient is premedicated prior to CD19-directed genetically modified autologous T cell immunotherapy infusion by oral administration of acetaminophen at a dose between about 500-1000 mg, about 600-1000 mg, about 700-1000 mg, about 800-1000 mg, about 900-1000 mg, about 500-900 mg, about 500-800 mg, about 500-700 mg, about 500-600 mg, about 600-900 mg, about 600-800 mg, about 600-700 mg, about 700-900 mg, about 700-800 mg, or about 800-900 mg. In some embodiments, the patient is premedicated prior to CD19-directed genetically modified autologous T cell immunotherapy infusion by oral administration of acetaminophen at a dose of about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg or about 1000 mg.

In some embodiments, the patient is premedicated prior to CD19-directed genetically modified autologous T cell immunotherapy infusion by administration of acetaminophen 650 mg by mouth and diphenhydramine 12.5 mg intravenously or by mouth approximately 1 hour before CD19-directed genetically modified autologous T cell immunotherapy infusion.

In some embodiments, the prophylactic use of systemic steroids is avoided as it may interfere with the activity of CD19-directed genetically modified autologous T cell immunotherapy.

Preparation of CD19-Directed Genetically Modified Autologous T Cell Immunotherapy for Infusion The timing of CD19-directed genetically modified autologous T cell immunotherapy thaw and infusion is coordinated. In some embodiments, the infusion time is confirmed in advance, and the start time of CD19-directed genetically modified autologous T cell immunotherapy thaw is adjusted such that it will be available for infusion when the patient is ready.

In some embodiments, the patient identity is confirmed prior to CD19-directed genetically modified autologous T cell immunotherapy thaw. Prior to CD19-directed genetically modified autologous T cell immunotherapy preparation, patient's identity is matched with the patient identifiers on the CD19-directed genetically modified autologous T cell immunotherapy cassette. In some embodiments, the CD19-directed genetically modified autologous T cell immunotherapy product bag is not removed from the cassette if the information on the patient-specific label does not match the intended patient.

In some embodiments, once patient identification is confirmed, CD19-directed genetically modified autologous T cell immunotherapy product bag is removed from the cassette and the patient information on the cassette label is confirmed to match the bag label.

In some embodiments, the method comprises inspecting the product bag for any breaches of container integrity such as breaks or cracks before thawing. In some embodiments, the infusion bag is placed inside a second sterile bag per local guidelines.

In some embodiments, the method comprises thawing the CD19-directed genetically modified autologous T cell immunotherapy at approximately 37° C. using either a water bath or dry thaw method until there is no visible ice in the infusion bag. In some embodiments, the method comprises mixing or agitating the contents of the bag to disperse clumps of cellular material. In some embodiments, the contents of the bag are gently mixed or agitated. In some embodiments, the method comprises inspecting the bag for the presence of visible cell clumps remaining and mixing or agitation is continued. Small clumps of cellular material should disperse with gentle manual mixing. In some embodiments, the method does not comprise a wash, spin down, and/or re-suspension of CD19-directed genetically modified autologous T cell immunotherapy in new media prior to infusion.

In some embodiments, once thawed, CD19-directed genetically modified autologous T cell immunotherapy may be stored at room temperature (20° C. to 25° C.) for up to 3 hours.

Administration

In some embodiments, the presently disclosed methods of administration of CD19-directed genetically modified autologous T cell immunotherapy comprise on or more of the following as steps or as considerations:

Ensure that tocilizumab and emergency equipment are available prior to infusion and during the recovery period.

Do NOT use a leukodepleting filter.

Central venous access is recommended for the infusion of CD19-directed genetically modified autologous T cell immunotherapy.

Confirm the patient's identity matches the patient identifiers on the CD19-directed genetically modified autologous T cell immunotherapy product bag.

Prime the tubing with normal saline prior to infusion.

Infuse the entire contents of the CD19-directed genetically modified autologous T cell immunotherapy bag within 30 minutes by either gravity or a peristaltic pump. CD19-directed genetically modified autologous T cell immunotherapy is stable at room temperature for up to 3 hours after thaw.

Gently agitate the product bag during CD19-directed genetically modified autologous T cell immunotherapy infusion to prevent cell clumping.

After the entire content of the product bag is infused, rinse the tubing with normal saline at the same infusion rate to ensure all product is delivered.

CD19-directed genetically modified autologous T cell immunotherapy contains human blood cells that are genetically modified with replication incompetent retroviral vector. Follow universal precautions and local biosafety guidelines for handling and disposal to avoid potential transmission of infectious diseases.

Monitoring

In some embodiments, administration of CD19-directed genetically modified autologous T cell immunotherapy occurs at a certified healthcare facility.

In some embodiments, the methods disclosed herein comprise monitoring patients at least daily for 7 days at the certified healthcare facility following infusion for signs and symptoms of CRS and neurologic toxicities. In some embodiments, the methods disclosed herein comprise monitoring patients at least daily for 10 days at the certified healthcare facility following infusion for signs and symptoms of CRS and neurologic toxicities.

In some embodiments, patients are instructed to remain within proximity of the certified healthcare facility for at least 4 weeks following infusion.

Management of Severe Adverse Reactions

In some embodiments, the method comprises management of adverse reactions. In some embodiments, the adverse reaction is selected from the group consisting of cytokine release syndrome (CRS), a neurologic toxicity, a hypersensitivity reaction, a serious infection, a cytopenia and hypogammaglobulinemia.

In some embodiments, the signs and symptoms of adverse reactions are selected from the group consisting of fever, hypotension, tachycardia, hypoxia, and chills, include cardiac arrhythmias (including atrial fibrillation and ventricular tachycardia), cardiac arrest, cardiac failure, renal insufficiency, capillary leak syndrome, hypotension, hypoxia, organ toxicity, hemophagocytic lymphohistiocytosis/macrophage activation syndrome (HLH/MAS), seizure, encephalopathy, headache, tremor, dizziness, aphasia, delirium, insomnia anxiety, anaphylaxis, febrile neutropenia, thrombocytopenia, neutropenia, and anemia.

Cytokine Release Syndrome

In some embodiments, the method comprises identifying CRS based on clinical presentation. In some embodiments, the method comprises evaluating for and treating other causes of fever, hypoxia, and hypotension. If CRS is observed or suspected, manage according to the recommendations in Table 1. Patients who experience ≥Grade 2 CRS (e.g., hypotension, not responsive to fluids, or hypoxia requiring supplemental oxygenation) should be monitored with continuous cardiac telemetry and pulse oximetry. In some embodiments, for patients experiencing severe CRS, consider performing an echocardiogram to assess cardiac function. For severe or life-threatening CRS, intensive care supportive therapy may be considered. In some embodiments, a biosimilar or equivalent of tocilizumab may be used instead of tocilizumab in the methods disclosed herein.

TABLE 1

| CRS Grading and Management Guidance | | |
|---|---|---|
| CRS Grade (a) | Tocilizumab | Corticosteroids |
| Grade 1<br>Symptoms require symptomatic treatment only (e.g., fever, nausea, fatigue, headache, myalgia, malaise). | N/A | N/A |
| Grade 2<br>Symptoms require and respond to moderate intervention.<br>Oxygen requirement less than 40% $FiO_2$ or hypotension responsive to fluids or low-dose of one vasopressor or Grade 2 organ toxicity (b). | Administer tocilizumab (c) 8 mg/kg IV over 1 hour (not to exceed 800 mg).<br>Repeat tocilizumab every 8 hours as needed if not responsive to IV fluids or increasing supplemental oxygen.<br>Limit to a maximum of 3 doses in a 24-hour period; maximum total of 4 doses if no clinical improvement in the signs and symptoms of CRS. | Manage per Grade 3 if no improvement within 24 hours after starting tocilizumab. |
| Grade 3<br>Symptoms require and respond to aggressive intervention.<br>Oxygen requirement greater than or equal to 40% $FiO_2$ or hypotension requiring high-dose or multiple vasopressors or Grade 3 organ toxicity or Grade 4 transaminitis. | Per Grade 2 | Administer methylprednisolone 1 mg/kg IV twice daily or equivalent dexamethasone (e.g., 10 mg IV every 6 hours).<br>Continue corticosteroids use until the event is Grade 1 or less, then taper over 3 days.<br>If not improving, manage as Grade 4. |
| Grade 4<br>Life-threatening symptoms.<br>Requirements for ventilator support, continuous veno-venous hemodialysis (CVVHD) or<br>Grade 4 organ toxicity (excluding transaminitis). | Per Grade 2 | Administer methylprednisolone 1000 mg IV per day for 3 days; if improves, then manage as above.<br>Consider alternate immunosuppressants if no improvement or if condition worsens. |

(a) Lee D W et al., (2014). Current concepts in the diagnosis and management of cytokine release syndrome. Blood. 2014 Jul. 10; 124(2): 188-195.
(b) Refer to Table 2 for management of neurologic toxicity.
(c) Refer to ACEMTRA ® (tocilizumab) Prescribing Information for details, https://www.gene.com/download/pdf/actemra_prescribing.pdf (last accessed Oct. 18, 2017). Initial U.S. approval is indicated to be in 2010.

Neurologic Toxicity

In some embodiments, the method comprises monitoring patients for signs and symptoms of neurologic toxicities (Table 2). In some embodiments, the method comprises ruling out other causes of neurologic symptoms. Patients who experience Grade 2 neurologic toxicities should be monitored with continuous cardiac telemetry and pulse oximetry. Provide intensive care supportive therapy for severe or life threatening neurologic toxicities. Consider non-sedating, anti-seizure medicines (e.g., levetiracetam) for seizure prophylaxis for any u Grade 2 neurologic toxicities.

TABLE 2

| Neurologic Toxicity Grading and Management Guidance | | |
|---|---|---|
| Grading Assessment | Concurrent CRS | No concurrent CRS |
| Grade 2 | Administer tocilizumab per Table 1 for management of Grade 2 CRS.<br>If no improvement within 24 hours after starting tocilizumab, administer dexamethasone 10 mg IV every 6 hours if not already taking other steroids.<br>Continue dexamethasone use until the event is Grade 1 or less, then taper over 3 days. | Administer dexamethasone 10 mg IV every 6 hours.<br>Continue dexamethasone use until the event is Grade 1 or less, then taper over 3 days. |
| | Consider non-sedating, anti-seizure medicines (e.g., levetiracetam) for seizure prophylaxis. | |

TABLE 2-continued

| Neurologic Toxicity Grading and Management Guidance | | |
|---|---|---|
| Grading Assessment | Concurrent CRS | No concurrent CRS |
| Grade 3 | Administer tocilizumab per Table 1 for management of Grade 2 CRS. In addition, administer dexamethasone 10 mg IV with the first dose of tocilizumab and repeat dose every 6 hours. Continue dexamethasone use until the event is Grade 1 or less, then taper over 3 days. | Administer dexamethasone 10 mg IV every 6 hours. Continue dexamethasone use until the event is Grade 1 or less, then taper over 3 days. |
| | Consider non-sedating, anti-seizure medicines (e.g., levetiracetam) for seizure prophylaxis. | |
| Grade 4 | Administer tocilizumab per Table 1 for management of Grade 2 CRS. Administer methylprednisolone 1000 mg IV per day with first dose of tocilizumab and continue methylprednisolone 1000 mg IV per day for 2 more days; if improves, then manage as above. | Administer methylprednisolone 1000 mg IV per day for 3 days; if improves, then manage as above. |
| | Consider non-sedating, anti-seizure medicines (e.g., levetiracetam) for seizure prophylaxis. | |

Dosage Forms And Strengths

In some embodiments, CD19-directed genetically modified autologous T cell immunotherapy is available as a cell suspension for infusion.

In some embodiments, a single dose of CD19-directed genetically modified autologous T cell immunotherapy comprises a target dose between about $1\times10^6$ and about $2\times10^6$ CAR-positive viable T cells per kg of body weight (or maximum of $2\times10^8$ CAR-positive viable T cells for patients 100 kg and above) in approximately 68 mL suspension in an infusion bag. In some embodiments, the CD19-directed genetically modified autologous T cell immunotherapy is axicabtagene ciloleucel (YESCARTAR).

In some embodiments, a single dose of CD19-directed genetically modified autologous T cell immunotherapy is present in a container. Such container may be sterile. In some embodiments, the container is an infusion bag. In some embodiments, the infusion bag volume is about 100 mL, 150 mL, 200 mL, 250 mL, 300 mL, 500 mL, 750 mL, 1,000 mL, 1,500 mL, 2,000 mL or 3,000 mL.

Risk Evaluation and Mitigation Strategy (REMS)

Because of the risk of CRS and neurologic toxicities, in some embodiments, CD19-directed genetically modified autologous T cell immunotherapy is available through a restricted program under a Risk Evaluation and Mitigation Strategy (REMS). Typical components of the REMS are:

- Healthcare facilities that dispense and administer CD19-directed genetically modified autologous T cell immunotherapy must be enrolled and comply with the REMS requirements.
- Certified healthcare facilities must have on-site, immediate access to tocilizumab, and ensure that a minimum of two doses of tocilizumab are available for each patient for infusion within 2 hours after CD19-directed genetically modified autologous T cell immunotherapy infusion, if needed for treatment of CRS.
- Certified healthcare facilities must ensure that healthcare providers who prescribe, dispense or administer CD19-directed genetically modified autologous T cell immunotherapy are trained about the management of CRS and neurologic toxicities.

Cytokine Release Syndrome (CRS)

In some embodiments, the health care facility ensures that two doses of tocilizumab are available prior to infusion of CD19-directed genetically modified autologous T cell immunotherapy. In some embodiments, the health care facility ensures that four doses of tocilizumab are available prior to infusion of CD19-directed genetically modified autologous T cell immunotherapy. In some embodiments, the method comprises monitoring patients at least daily for 7 days at the certified healthcare facility following infusion for signs and symptoms of CRS. In some embodiments, the method comprises monitoring patients at least daily for 7-10 days at the certified healthcare facility following infusion for signs and symptoms of CRS. In some embodiments, the method comprises monitoring patients at least daily for 8 days at the certified healthcare facility following infusion for signs and symptoms of CRS. In some embodiments, the method comprises monitoring patients at least daily for 9 days at the certified healthcare facility following infusion for signs and symptoms of CRS. In some embodiments, the method comprises monitoring patients at least daily for 10 days at the certified healthcare facility following infusion for signs and symptoms of CRS. In some embodiments, the method comprises monitoring patients for signs or symptoms of CRS for 4 weeks after infusion. In some embodiments, the method comprises counseling patients to seek immediate medical attention should signs or symptoms of CRS occur at any time. In some embodiments, the method comprises instituting treatment with supportive care, tocilizumab or tocilizumab and corticosteroids as indicated at the first sign of CRS.

Neurologic Toxicities

In some embodiments, the method comprises monitoring patients at least daily for 7 days at the certified healthcare facility following infusion for signs and symptoms of neurologic toxicities. In some embodiments, the method comprises monitoring patients at least daily for 7-10 days at the certified healthcare facility following infusion for signs and symptoms of CRS. In some embodiments, the method comprises monitoring patients at least daily for 10 days at the certified healthcare facility following infusion for signs and symptoms of CRS. In some embodiments, the method comprises monitoring patients for signs or symptoms of neurologic toxicities for 4 weeks after infusion and treat promptly.

Hypersensitivity Reactions

Allergic reactions may occur with the infusion of CD19-directed genetically modified autologous T cell immunotherapy. In some embodiments, serious hypersensitivity reactions including anaphylaxis, may be due to dimethyl sulfoxide (DMSO) or residual gentamicin in CD19-directed genetically modified autologous T cell immunotherapy.

Viral Reactivation

In some embodiments, Hepatitis B virus (HBV) reactivation, in some cases resulting in fulminant hepatitis, hepatic failure and death, may occur in patients treated with drugs directed against B cells. In some embodiments, the method comprises performing screening for HBV, HCV, and HIV in accordance with clinical guidelines before collection of cells for manufacturing.

Prolonged Cytopenias

In some embodiments, patients may exhibit cytopenias for several weeks following lymphodepleting chemotherapy and CD19-directed genetically modified autologous T cell immunotherapy infusion. In some embodiments, the method comprises monitoring blood counts after CD19-directed genetically modified autologous T cell immunotherapy infusion.

Hypogammaglobulinemia

In some embodiments, B-cell aplasia and hypogammaglobulinemia may occur in patients receiving treatment with CD19-directed genetically modified autologous T cell immunotherapy. In some embodiments, the method comprises monitoring immunoglobulin levels after treatment with CD19-directed genetically modified autologous T cell immunotherapy and managing using infection precautions, antibiotic prophylaxis and immunoglobulin replacement.

In some embodiments, vaccination with live virus vaccines is not recommended for at least 6 weeks prior to the start of lymphodepleting chemotherapy, during CD19-directed genetically modified autologous T cell immunotherapy treatment, and until immune recovery following treatment with CD19-directed genetically modified autologous T cell immunotherapy.

Secondary Malignancies

In some embodiments, patients treated with CD19-directed genetically modified autologous T cell immunotherapy may develop secondary malignancies. In some embodiments, the method comprises monitoring life-long for secondary malignancies.

Tumour Lysis Syndrome (TLS)

Patients treated with CD19-directed genetically modified autologous T cell immunotherapy may develop TLS, which may be severe. To minimise risk of TLS, in some embodiments, the method comprises evaluating patients for elevated uric acid or high tumour burden and administering allopurinol, or an alternative prophylaxis, prior to axicabtagene ciloleucel infusion. Signs and symptoms of TLS should be monitored and events managed according to standard guidelines.

Effects on Ability to Drive and Use Machines

Due to the potential for neurologic events, including altered mental status or seizures, patients receiving CD19-directed genetically modified autologous T cell immunotherapy are at risk for altered or decreased consciousness or coordination in the 8 weeks following CD19-directed genetically modified autologous T cell immunotherapy infusion. In some embodiments, the method comprises advising patients to refrain from driving and engaging in hazardous occupations or activities, such as operating heavy or potentially dangerous machinery, during this initial period.

Storage and Handling

In some embodiments, CD19-directed genetically modified autologous T cell immunotherapy is supplied in an infusion bag containing approximately 68 mL of frozen suspension of genetically modified autologous T cells in 5% DMSO and 2.5% albumin (human). In some embodiments, CD19-directed genetically modified autologous T cell immunotherapy is supplied in an infusion bag containing approximately 68 mL of frozen suspension of genetically modified autologous T cells in 5% DMSO and 2.5% albumin (human) (NDC 71287-119-01). In some embodiments, CD19-directed genetically modified autologous T cell immunotherapy comprises Cryostor CS10. In some embodiments, CD19-directed genetically modified autologous T cell immunotherapy comprises 300 mg sodium per infusion. In some embodiments, CD19-directed genetically modified autologous T cell immunotherapy is supplied in an infusion bag containing approximately 50-100 mL, 50-90 mL, 50-80 mL, 50-70 mL, 60-70 mL, 60-75 mL, or 65-75 mL, of suspension of genetically modified autologous T cells in 5% DMSO and 2.5% albumin (human). In some embodiments, CD19-directed genetically modified autologous T cell immunotherapy is supplied in an infusion bag containing less than 100 mL, less than 90 mL, less than 80 mL, less than 70 mL, less than 70 mL, less than 72 mL, or less than 75 mL, of suspension of genetically modified autologous T cells in 5% DMSO and 2.5% albumin (human). In some embodiments, CD19-directed genetically modified autologous T cell immunotherapy is supplied in an infusion bag containing greater than 50 mL, greater than 60 mL, greater than 65 mL, greater than 66 mL, greater than 67 mL, or greater than 68 mL, of suspension of genetically modified autologous T cells in 5% DMSO and 2.5% albumin (human). In some embodiments, the suspension is frozen.

In some embodiments, the CD19-directed genetically modified autologous T cell immunotherapy infusion bag is supplied in ethylene-vinyl acetate cryostorage bag with sealed addition tube and two available spike ports, containing approximately 68 mL of cell dispersion.

In some embodiments, the CD19-directed genetically modified autologous T cell immunotherapy infusion bag is individually packed in a metal cassette. In some embodiments, the CD19-directed genetically modified autologous T cell immunotherapy infusion bag is individually packed in a metal cassette (NDC 71287-119-02). In some embodiments, the CD19-directed genetically modified autologous T cell immunotherapy infusion bag is stored in the vapor phase of liquid nitrogen. In some embodiments, the CD19-directed genetically modified autologous T cell immunotherapy infusion bag is supplied in a liquid nitrogen dry shipper.

In some embodiments, the method comprises matching the identity of the patient with the patient identifiers on the cassette and infusion bag upon receipt. In some embodiments, CD19-directed genetically modified autologous T cell immunotherapy is stored frozen in the vapor phase of liquid nitrogen (less than or equal to minus 150° C.). In some embodiments, the CD19-directed genetically modified autologous T cell immunotherapy is thaw before using.

EXAMPLES

Example 1: Clinical Studies of Relapsed or Refractory Large B-Cell Lymphoma

A single-arm, open-label, multicenter trial evaluated the efficacy of a single infusion of Axi-cel™ (YESCARTA®) in adult patients with relapsed or refractory aggressive B-cell non-Hodgkin lymphoma. Eligible patients had refractory disease to the most recent therapy or relapse within 1 year after autologous hematopoietic stem cell transplantation (HSCT). The study excluded patients with prior allogeneic HSCT, any history of central nervous system lymphoma, ECOG performance status of 2 or greater, absolute lymphocyte count less than 100/μL, creatinine clearance less than 60 mL/min, hepatic transaminases more than 2.5 times the upper limit of normal, cardiac ejection fraction less than 50%, or active serious infection.

Following lymphodepleting chemotherapy, Axi-cel™ was administered as a single IV infusion at a target dose of $2\times10^6$ CAR-positive viable T cells/kg (maximum permitted dose: $2\times10^8$ cells). The lymphodepleting regimen consisted of cyclophosphamide 500 mg/m$^2$ IV and fludarabine 30 mg/m$^2$ IV, both given on the fifth, fourth, and third day before Axi-cel™. Bridging chemotherapy between leukapheresis and lymphodepleting chemotherapy was not permitted. All patients were hospitalized for Axi-cel™ infusion and for a minimum of 7 days afterward.

Of 111 patients who underwent leukapheresis, 101 received Axi-cel™. Of the patients treated, the median age was 58 years (range: 23 to 76), 67% were male, and 89% were white. Most (76%) had DLBCL, 16% had transformed follicular lymphoma, and 8% had primary mediastinal large B-cell lymphoma. The median number of prior therapies was 3 (range: 1 to 10), 77% of the patients had refractory disease to a second or greater line of therapy, and 21% had relapsed within 1 year of autologous HSCT.

One out of 111 patients did not receive the product due to manufacturing failure. Nine other patients were not treated, primarily due to progressive disease or serious adverse reactions following leukapheresis. The median time from leukapheresis to product delivery was 17 days (range: 14 to 51 days), and the median time from leukapheresis to infusion was 24 days (range: 16 to 73 days). The median dose was $2.0\times10^6$ CAR-positive viable T cells/kg (range: 1.1 to $2.2\times10^6$ cells/kg).

Efficacy was established on the basis of complete remission (CR) rate and duration of response (DOR), as determined by an independent review committee (Table 3 and Table 4). The median time to response was 0.9 months (range: 0.8 to 6.2 months). Response durations were longer in patients who achieved CR, as compared to patients with a best response of partial remission (PR) (Table 4). Of the 52 patients who achieved CR, 14 initially had stable disease (7 patients) or PR (7 patients), with a median time to improvement of 2.1 months (range: 1.6 to 5.3 months).

TABLE 3

| Response Rate | |
|---|---|
| | Recipients of Axi-cel ™ (N = 101) |
| Objective Response Rate[a] | 73 (72%) |
| (95% CI) | (62, 81) |
| Complete Remission Rate | 52 (51%) |
| (95% CI) | (41, 62) |
| Partial Remission Rate | 21 (21%) |
| (95% CI) | (13, 30) |

CI, confidence interval.

[a]Per 2007 revised International Working Group criteria, as assessed by the independent review committee.

TABLE 4

| Duration of Response | |
|---|---|
| | From N of 101 |
| Number of Responders | 73 |
| DOR (Months)[a] | |
| Median[b] | 9.2 |
| (95% CI) | (5.4, NE) |
| Range[c] | 0.03+, 14.4+ |
| DOR if Best Response is CR (Months) | |
| Median[b] | NE |
| (95% CI) | (8.1, NE) |
| Range | 0.4, 14.4+ |
| DOR if Best Response is PR (Months) | |
| Median[b] | 2.1 |
| (95% CI) | (1.3, 5.3) |
| Range | 0.03+, 8.4+ |
| Median Follow-up for DOR (Months)[a,b] | 7.9 |

CR, complete remission; DOR, duration of response; NE, not estimable; PR, partial remission.

[a]Among all responders. DOR is measured from the date of first objective response to the date of progression or death from relapse or toxicity.

[b]Kaplan-Meier estimate.

[c]A + sign indicates a censored value.

Example 2: Pharmacodynamics and Pharmacokinetics after Axi-Cel™ Infusion

After Axi-cel™ infusion, pharmacodynamic responses were evaluated over a 4-week interval by measuring transient elevation of cytokines, chemokines and other molecules in blood. Levels of cytokines and chemokines such as IL-6, IL-8, IL-10, IL-15, TNF-α, IFN-γ, and sIL2Rα were analyzed. Peak elevation was observed within the first 14 days after infusion, and levels generally returned to baseline within 28 days. Due to the on-target effect of Axi-cel™, a period of B-cell aplasia is expected.

Following infusion of Axi-cel™, anti-CD19 CAR T cells exhibited an initial rapid expansion followed by a decline to near baseline levels by 3 months. Peak levels of anti-CD 19 CAR T cells occurred within the first 7-14 days after Axi-cel™ infusion. Age (range: 23-76 years) and gender had no significant impact on $AUC_{(0-28d)}$ and Cmax of Axi-cel™.

The number of anti-CD19 CAR T cells in blood was positively associated with objective response (complete remission (CR) or partial remission (PR)). The median anti-CD19 CAR T-cell Cmax levels in responders (n=73) were 205% higher compared to the corresponding level in nonresponders (n=23) (43.6 cells/μL vs 21.2 cells/μL). Median AUC Day 0-28 in responding patients (n=73) was 251% of the corresponding level in nonresponders (n=23) (557.1 days*cells/μL vs. 222.0 days*cells/μL).

Some patients required tocilizumab and corticosteroids for management of CRS and neurologic toxicities. Patients treated with tocilizumab (n=44) had 262% and 232% higher anti-CD19 CAR T cells as measured by $AUC_{(0-28d)}$ and Cmax respectively, as compared to patients who did not receive tocilizumab (n=57). Similarly, patients that received corticosteroids (n=26) had 217% and 155% higher $AUC_{(0-28d)}$ and Cmax compared to patients who did not receive corticosteroids (n=75).

Example 3: Management of Adverse Reactions after CD19-Directed Genetically Modified Autologous T Cell Immunotherapy Because clinical trials are conducted under widely varying conditions, adverse reaction rates observed in the clinical trials of a drug cannot be directly compared to rates in the clinical trials of another drug and may not reflect the rates observed in practice.

The safety data described in this section reflect exposure to Axi-cel™ in the clinical trial (Study 1) in which 108 patients with relapsed/refractory B-cell NHL received CAR-positive T cells based on a recommended dose which was weight-based. Patients with a history of CNS disorders (such as seizures or cerebrovascular ischemia) or autoimmune disease requiring systemic immunosuppression were ineligible. The median duration of follow up was 8.7 months. The median age of the study population was 58 years (range: 23 to 76 years); 68% were men. The baseline ECOG performance status was 43% with ECOG 0, and 57% with ECOG 1.

The most common adverse reactions (incidence ≥20%) include CRS, fever, hypotension, encephalopathy, tachycardia, fatigue, headache, decreased appetite, chills, diarrhea, febrile neutropenia, infections-pathogen unspecified, nausea, hypoxia, tremor, cough, vomiting, dizziness, constipation, and cardiac arrhythmias. Serious adverse reactions occurred in 52% of patients. The most common serious adverse reactions (>2%) include encephalopathy, fever, lung infection, febrile neutropenia, cardiac arrhythmia, cardiac failure, urinary tract infection, renal insufficiency, aphasia, cardiac arrest, *Clostridium difficile* infection, delirium, hypotension, and hypoxia.

The most common (≥10%) Grade 3 or higher reactions include febrile neutropenia, fever, CRS, encephalopathy, infections-pathogen unspecified, hypotension, hypoxia and lung infections.

Forty-five percent (49/108) of patients received tocilizumab after infusion of Axi-cel™.

Table 5 summarizes the adverse reactions that occurred in at least 10% of patients treated with Axi-cel™ and Table 6 describes the laboratory abnormalities of Grade 3 or 4 that occurred in at least 10% of patients.

TABLE 5

Summary of Adverse Reactions Observed in at Least 10% of the Patients Treated with Axi-cel ™ in Study 1

| Adverse Reaction | Any Grade (%) | Grade 3 or Higher (%) |
|---|---|---|
| Cardiac Disorders | | |
| Tachycardia[a] | 57 | 2 |
| Arrhythmia[b] | 23 | 7 |
| Gastrointestinal Disorders | | |
| Diarrhea | 38 | 4 |
| Nausea | 34 | 0 |
| Vomiting | 26 | 1 |
| Constipation | 23 | 0 |
| Abdominal pain[c] | 14 | 1 |
| Dry mouth | 11 | 0 |
| General Disorders And Administration Site Conditions | | |
| Fever | 86 | 16 |
| Fatigue[d] | 46 | 3 |
| Chills | 40 | 0 |
| Edema[e] | 19 | 1 |
| Immune System Disorders | | |
| Cytokine release syndrome | 94 | 13 |
| Hypogammaglobulinemia[f] | 15 | 0 |

TABLE 5-continued

Summary of Adverse Reactions Observed in at Least 10% of the Patients Treated with Axi-cel ™ in Study 1

| Adverse Reaction | Any Grade (%) | Grade 3 or Higher (%) |
|---|---|---|
| Infections And Infestations | | |
| Infections-pathogen unspecified | 26 | 16 |
| Viral infections | 16 | 4 |
| Bacterial Infections | 13 | 9 |
| Investigations | | |
| Decreased appetite | 44 | 2 |
| Weight decreased | 16 | 0 |
| Dehydration | 11 | 3 |
| Musculoskelatal And Connective Tissue Disorders | | |
| Motor dysfunction[g] | 19 | 1 |
| Pain in extremity[h] | 17 | 2 |
| Back pain | 15 | 1 |
| Muscle pain | 14 | 1 |
| Arthralgia | 10 | 0 |
| Nervous System Disorders | | |
| Encephalopathy[i] | 57 | 29 |
| Headache[j] | 45 | 1 |
| Tremor | 31 | 2 |
| Dizziness[k] | 21 | 1 |
| Aphasia[l] | 18 | 6 |
| Psychiatric Disorders | | |
| Delirium[m] | 17 | 6 |
| Respiratory, Thoracic And Mediastinal Disorders | | |
| Hypoxia[n] | 32 | 11 |
| Cough[o] | 30 | 0 |
| Dyspnea[p] | 19 | 3 |
| Pleural effusion | 13 | 2 |
| Renal and Urinary Disorders | | |
| Renal insufficiency | 12 | 5 |
| Vascular Disorders | | |
| Hypotension[q] | 57 | 15 |
| Hypertension | 15 | 6 |
| Thrombosis[r] | 10 | 1 |

The following events were also counted in the incidence of CRS: tachycardia, arrhythmia, fever, chills, hypoxia, renal insufficiency, and hypotension.

[a]Tachycardia includes tachycardia, sinus tachycardia.

[b]Arrhythmia includes arrhythmia, atrial fibrillation, atrial flutter, atrioventricular block, bundle branch block right, electrocardiogram QT prolonged, extra-systoles, heart rate irregular, supraventricular extra systoles, supraventricular tachycardia, ventricular arrhythmia, ventricular tachycardia.

[c]Abdominal pain includes abdominal pain, abdominal pain lower, abdominal pain upper.

[d]Fatigue includes fatigue, malaise.

[e]Edema includes face edema, generalized edema, local swelling, localized edema, edema, edema genital, edema peripheral, periorbital edema, peripheral swelling, scrotal edema.

[f]Hypogammaglobulinemia includes hypogammaglobulinemia, blood immunoglobulin D decreased, blood immunoglobulin G decreased.

[g]Motor dysfunction includes muscle spasms, muscular weakness.

[h]Pain in extremity includes pain not otherwise specified, pain in extremity.

[i]Encephalopathy includes cognitive disorder, confusional state, depressed level of consciousness, disturbance in attention, encephalopathy, hypersomnia, leukoencephalopathy, memory impairment, mental status changes, paranoia, somnolence, stupor.

[j]Headache includes headache, head discomfort, sinus headache, procedural headache.

[k]Dizziness includes dizziness, presyncope, syncope.

[l]Aphasia includes aphasia, dysphasia.

[m]Delirium includes agitation, delirium, delusion, disorientation, hallucination, hyperactivity, irritability, restlessness.

[n]Hypoxia includes hypoxia, oxygen saturation decreased.

[o]Cough includes cough, productive cough, upper-airway cough syndrome.

[p]Dyspnea includes acute respiratory failure, dyspnea, orthopnea, respiratory distress.

[q]Hypotension includes diastolic hypotension, hypotension, orthostatic hypotension.

[r]Thrombosis includes deep vein thrombosis, embolism, embolism venous, pulmonary embolism, splenic infarction, splenic vein thrombosis, subclavian vein thrombosis, thrombosis, thrombosis in device.

Other clinically important adverse reactions that occurred in less than 10% of patients treated with Axi-cel™ include the following:

Blood and lymphatic system disorders: Coagulopathy (2%)

Cardiac disorders: Cardiac failure (6%) and cardiac arrest (4%)

Immune system disorders: Hemophagocytic lymphohistiocytosis/macrophage activation syndrome (HLH/MAS) (1%), hypersensitivity (1%)

Infections and infestations disorders: Fungal infections (5%)

Nervous system disorders: Ataxia (6%), seizure (4%), dyscalculia (2%), and myoclonus (2%)

Respiratory, thoracic and mediastinal disorders: Pulmonary edema (9%)

Skin and subcutaneous tissue disorders: Rash (9%)

Vascular disorders: Capillary leak syndrome (3%)

Laboratory Abnormalities:

TABLE 6

Grade 3 or 4 Laboratory Abnormalities Occurring in ≥10% of Patients in Study 1 Following Treatment with Axi-cel based on CTCAE (N = 108)

| | Grades 3 or 4 (%) |
|---|---|
| Lymphopenia | 100 |
| Leukopenia | 96 |
| Neutropenia | 93 |
| Anemia | 66 |
| Thrombocytopenia | 58 |
| Hypophosphatemia | 50 |
| Hyponatremia | 19 |
| Uric acid increased | 13 |
| Direct Bilirubin increased | 13 |
| Hypokalemia | 10 |
| Alanine Aminotransferase increased | 10 |

Cytokine Release Syndrome

CRS, including fatal or life-threatening reactions, occurred following treatment with Axi-cel™. In Study 1, CRS occurred in 94% (101/108) of patients receiving Axi-cel™, including ≥Grade 3 (Lee grading system[1]) CRS in 13% (14/108) of patients. Among patients who died after receiving Axi-cel™, four had ongoing CRS events at the time of death. The median time to onset was 2 days (range: 1 to 12 days) and the median duration of CRS was 7 days (range: 2 to 58 days). Key manifestations of CRS include fever (78%), hypotension (41%), tachycardia (28%), hypoxia (22%), and chills (20%). Serious events that may be associated with CRS include cardiac arrhythmias (including atrial fibrillation and ventricular tachycardia), cardiac arrest, cardiac failure, renal insufficiency, capillary leak syndrome, hypotension, hypoxia, and hemophagocytic lymphohistiocytosis/macrophage activation syndrome (HLH/MAS).

Neurologic Toxicities

Neurologic toxicities, that were fatal or life-threatening, occurred following treatment with Axi-cel™. Neurologic toxicities occurred in 87% of patients. Ninety-eight percent of all neurologic toxicities occurred within the first 8 weeks of Axi-cel™ infusion, with a median time to onset of 4 days (range: 1 to 43 days). The median duration of neurologic toxicities was 17 days. Grade 3 or higher neurologic toxicities occurred in 31% of patients.

The most common neurologic toxicities included encephalopathy (57%), headache (44%), tremor (31%), dizziness (21%), aphasia (18%), delirium (17%), insomnia (9%) and anxiety (9%). Prolonged encephalopathy lasting up to 173 days was noted. Serious events including leukoencephalopathy and seizures occurred with Axi-cel™. Fatal and serious cases of cerebral edema have occurred in patients treated with Axi-cel™.

Serious Infections

Severe or life-threatening infections occurred in patients after Axi-cel™ infusion. In Study 1, infections (all grades) occurred in 38% of patients. Grade 3 or higher infections occurred in 23% of patients. Grade 3 or higher infections with an unspecified pathogen occurred in 16% of patients, bacterial infections in 9%, and viral infections in 4%. Axi-cel™ should not be administered to patients with clinically significant active systemic infections. Monitor patients for signs and symptoms of infection before and after Axi-cel™ infusion and treat appropriately. Administer prophylactic anti-microbials according to local guidelines.

Febrile neutropenia was observed in 36% of patients after Axi-cel™ infusion and may be concurrent with CRS. In the event of febrile neutropenia, evaluate for infection and manage with broad spectrum antibiotics, fluids and other supportive care as medically indicated.

Immunogenicity

Axi-cel™ has the potential to induce anti-product antibodies. The immunogenicity of Axi-cel™ has been evaluated using an enzyme-linked immunosorbent assay (ELISA) for the detection of binding antibodies against FMC63, the originating antibody of the anti-CD19 CAR. Three patients tested positive for pre-dose anti-FMC63 antibodies at baseline and months 1, 3, or 6 in Study 1. There is no evidence that the kinetics of initial expansion and persistence of Axi-cel™, or the safety or effectiveness of Axi-cel™, was altered in these patients.

In Study 1, Grade 3 or higher cytopenias not resolved by Day 30 following Axi-cel™ infusion occurred in (28%) of patients and included thrombocytopenia (18%), neutropenia (15%), and anemia (3%). Monitor blood counts after Axi-cel™ infusion.

In Study 1, hypogammaglobulinemia occurred in 15% of patients.

All publications, patents, patent applications, and references, including prescribing information, that are mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present invention. To the extent that any of the definitions or terms provided in the references incorporated by reference differ from the terms and discussion provided herein, the present terms and definitions control.

The invention claimed is:

1. A method for treating, high grade B-cell lymphoma in a patient comprising:

administering to the patient in need thereof an axicabtagene ciloleucel suspension by intravenous infusion at a dose between about $1\times10^6$ and about $2\times10^6$ CAR-positive viable T cells per kg body weight up to a maximum dose of about $2\times10^8$ CAR-positive viable T cells, wherein axicabtagene ciloleucel is a CD19-directed genetically modified autologous T cell immunotherapy, comprising the patient's own T cells harvested and genetically modified ex vivo by retroviral transduction to express a chimeric antigen receptor (CAR) comprising an anti-CD19 single chain variable fragment (scFv) linked to CD28 and CD3-zeta co-stimulatory domains.

2. The method of claim 1, wherein the intravenous infusion is for a time period between 15 and 120 minutes.

3. The method of claim 1, wherein the intravenous infusion is for a time period up to 30 minutes.

4. The method of claim 1, wherein between 50 and 100 mL of the axicabtagene ciloleucel suspension is administered.

5. The method of claim 1, wherein about 68 mL of the axicabtagene ciloleucel suspension is administered.

6. The method of claim 1, wherein the axicabtagene ciloleucel suspension is infused from an infusion bag.

7. The method of claim 6, wherein the infusion bag is agitated during the infusion.

8. The method of claim 1, wherein the axicabtagene ciloleucel suspension is administered within 3 hours after thawing.

9. The method of claim 1, wherein the axicabtagene ciloleucel suspension further comprises albumin.

10. The method of claim 9, wherein albumin is present in an amount of about 2-3% (v/v).

11. The method of claim 1, wherein the axicabtagene ciloleucel suspension further comprises DMSO.

12. The method of claim 1, further comprising monitoring the patient for symptoms of cytokine release syndrome (CRS) daily for 7-10 days following the infusion, and administering to the patient a steroid:

(a) when CRS Grade 3 is observed; or (b) when CRS Grade 2 is observed and treated but CRS symptoms do not improve after 24 hours.

13. The method of claim 12, wherein the monitoring is daily for 7 days following the infusion.

14. The method of claim 12, wherein the steroid is a corticosteroid.

15. The method of claim 14, wherein the corticosteroid is methylprednisolone or dexamethasone.

* * * * *